United States Patent
Ruchti et al.

(10) Patent No.: US 10,842,935 B2
(45) Date of Patent: *Nov. 24, 2020

(54) SYSTEMS AND METHODS FOR DETERMINING INSULIN THERAPY FOR A PATIENT

(71) Applicant: MONARCH MEDICAL TECHNOLOGIES, LLC, Charlotte, NC (US)

(72) Inventors: Timothy L. Ruchti, Gurnee, IL (US); William Patrick Burgess, Charlotte, NC (US); John Dumas, III, Libertyville, IL (US); Ronald Lisiecki, Libertyville, NC (US); Carol Dian Martin, Charlotte, NC (US); Laura Santana, Charlotte, NC (US); John Harrison Thornley, Charlotte, NC (US); Joanne Marie Watt, Tower Lakes, IL (US)

(73) Assignee: Monarch Medical Technologies, LLC, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,676

(22) Filed: Jul. 30, 2018

(65) Prior Publication Data
US 2018/0333535 A1 Nov. 22, 2018

Related U.S. Application Data

(63) Continuation of application No. 13/725,115, filed on Dec. 21, 2012, now Pat. No. 10,046,113.
(Continued)

(51) Int. Cl.
*A61M 5/172* (2006.01)
*G16H 50/20* (2018.01)
(Continued)

(52) U.S. Cl.
CPC ....... *A61M 5/1723* (2013.01); *A61B 5/14532* (2013.01); *A61B 5/7275* (2013.01);
(Continued)

(58) Field of Classification Search
CPC ......... A61M 5/1723; A61M 2005/1726; G06F 19/00; G06F 19/345; G06F 19/3456;
(Continued)

(56) References Cited

U.S. PATENT DOCUMENTS 5,422,125 A 6/1995 Skyler et al.
6,200,958 B1 3/2001 Odaka et al.
(Continued)

FOREIGN PATENT DOCUMENTS

KR 10-2010-0027165 A 3/2010
WO 2008057213 A2 5/2008
(Continued)

OTHER PUBLICATIONS

Extended European Search Report dated Jan. 2, 2020 for EP Application No. 19190466.3.
(Continued)

*Primary Examiner* — Tiffany Legette
(74) *Attorney, Agent, or Firm* — Dorsey & Whitney LLP

(57) ABSTRACT

In example methods and systems described, insulin therapy for a patient can be determined. At least one of a short-acting subcutaneous insulin dosage recommendation, a correction subcutaneous insulin dosage recommendation, an intravenous insulin dosage recommendation, a recommended amount of carbohydrates to be administered to the patient, or combinations thereof, can be determined. In addition, information indicating a confirmation of a nutrition intake for the patient, and a long-acting insulin-on-board for the patient can be received, and based on this information, a required long-acting subcutaneous or intravenous insulin dosage for
(Continued)

the patient can be determined. The short-acting subcutaneous or intravenous insulin dosage recommendation can be adjusted based, at least in part, on a difference between the long-acting insulin-on-board and the required long-acting subcutaneous or intravenous insulin dosage.

20 Claims, 20 Drawing Sheets

Related U.S. Application Data

(60) Provisional application No. 61/578,693, filed on Dec. 21, 2011.

(51) Int. Cl.
  *G06Q 50/22* (2018.01)
  *G06F 19/00* (2018.01)
  *A61B 5/00* (2006.01)
  *A61B 5/145* (2006.01)

(52) U.S. Cl.
  CPC ......... *G06F 19/3456* (2013.01); *G06Q 50/22* (2013.01); *G16H 50/20* (2018.01)

(58) Field of Classification Search
  CPC ........ G16H 40/63; G16H 20/17; G16H 50/20; G16G 50/20; G06Q 50/22; A61B 5/14532; A61B 5/7275
  See application file for complete search history.

(56) References Cited

U.S. PATENT DOCUMENTS

| | | |
|---|---|---|
| 7,291,107 B2 | 11/2007 | Hellwig et al. |
| 7,404,796 B2 | 7/2008 | Ginsberg |
| 7,704,226 B2 | 4/2010 | Mueller, Jr. et al. |
| 7,785,313 B2 | 8/2010 | Mastrototaro |
| 9,171,343 B1 | 10/2015 | Fischell et al. |
| 9,233,204 B2 | 1/2016 | Booth et al. |
| 9,483,619 B2 | 11/2016 | Fischell et al. |
| 9,486,580 B2 | 11/2016 | Booth et al. |
| 9,504,789 B2 | 11/2016 | Booth et al. |
| 9,604,002 B2 | 3/2017 | Booth et al. |
| 9,710,611 B2 | 7/2017 | Booth et al. |
| 9,773,096 B2 | 9/2017 | Booth et al. |
| 9,811,638 B2 | 11/2017 | Booth et al. |
| 9,886,556 B2 | 2/2018 | Booth et al. |
| 9,892,234 B2 | 2/2018 | Booth et al. |
| 9,892,235 B2 | 2/2018 | Booth et al. |
| 9,897,565 B1 | 2/2018 | Booth |
| 9,898,585 B2 | 2/2018 | Booth et al. |
| 10,046,113 B2 | 3/2018 | Ruchti et al. |
| 10,128,002 B2 | 11/2018 | Booth et al. |
| 10,255,992 B2 | 4/2019 | Booth et al. |
| 10,403,397 B2 | 9/2019 | Booth et al. |
| 10,410,740 B2 | 9/2019 | Booth et al. |
| 10,453,936 B2 | 10/2019 | Shu et al. |
| 2002/0041863 A1 | 4/2002 | Kojiro et al. |
| 2003/0224046 A1 | 12/2003 | Rao et al. |
| 2007/0078314 A1 | 4/2007 | Grounsell et al. |
| 2008/0306353 A1 | 12/2008 | Douglas et al. |
| 2009/0006061 A1 | 1/2009 | Thurkal et al. |
| 2009/0054754 A1 | 2/2009 | McMahon et al. |
| 2009/0177147 A1 | 7/2009 | Blomquist et al. |
| 2009/0253634 A1 | 10/2009 | Currie et al. |
| 2009/0281519 A1 | 11/2009 | Rao et al. |
| 2010/0017141 A1 | 1/2010 | Campbell et al. |
| 2010/0035794 A1 | 2/2010 | Richardson et al. |
| 2010/0094251 A1 | 4/2010 | Estes |
| 2010/0136133 A1 | 6/2010 | Moore et al. |
| 2010/0138197 A1 | 6/2010 | Sher |
| 2010/0174266 A1* | 7/2010 | Estes ............... G16H 20/17 604/504 |
| 2010/0185142 A1 | 7/2010 | Kamen et al. |
| 2010/0198142 A1* | 8/2010 | Sloan ............... G16H 20/10 604/66 |
| 2010/0204557 A1 | 8/2010 | Kiaie et al. |
| 2010/0292634 A1 | 11/2010 | Kircher, Jr. et al. |
| 2011/0034791 A1 | 2/2011 | Moerman |
| 2011/0098548 A1 | 4/2011 | Budiman et al. |
| 2011/0144586 A1 | 6/2011 | Michaud et al. |
| 2011/0152830 A1 | 6/2011 | Ruchti et al. |
| 2011/0307228 A1 | 12/2011 | Kasabov |
| 2013/0165901 A1 | 6/2013 | Ruchti et al. |
| 2015/0217053 A1 | 8/2015 | Booth et al. |
| 2015/0217054 A1 | 8/2015 | Booth et al. |
| 2015/0217055 A1 | 8/2015 | Booth et al. |
| 2016/0012204 A1 | 1/2016 | Booth et al. |
| 2016/0058944 A1 | 3/2016 | Booth et al. |
| 2016/0117481 A1 | 4/2016 | Booth et al. |
| 2017/0007761 A1 | 1/2017 | Booth et al. |
| 2017/0024543 A1 | 1/2017 | Booth et al. |
| 2017/0053101 A1 | 2/2017 | Booth et al. |
| 2017/0068802 A1 | 3/2017 | Booth et al. |
| 2017/0076067 A1 | 3/2017 | Booth et al. |
| 2017/0124286 A1 | 5/2017 | Booth et al. |
| 2017/0165425 A9 | 6/2017 | Ruchti et al. |
| 2017/0228518 A1 | 8/2017 | Booth et al. |
| 2017/0281098 A1 | 10/2017 | Booth et al. |
| 2017/0344725 A1 | 11/2017 | Booth et al. |
| 2017/0351842 A1 | 12/2017 | Booth et al. |
| 2018/0144818 A1 | 5/2018 | Booth et al. |
| 2018/0226149 A1 | 8/2018 | Booth et al. |
| 2018/0366217 A1 | 12/2018 | Booth et al. |
| 2019/0019572 A1 | 1/2019 | Booth et al. |
| 2019/0019577 A1 | 1/2019 | Booth et al. |
| 2019/0074078 A1 | 3/2019 | Booth et al. |
| 2019/0180858 A1 | 6/2019 | Booth et al. |
| 2019/0198146 A1 | 6/2019 | Booth et al. |
| 2019/0326005 A1 | 10/2019 | Booth et al. |
| 2019/0348157 A1 | 11/2019 | Booth et al. |
| 2019/0348166 A1 | 11/2019 | Booth et al. |
| 2020/0027544 A1 | 1/2020 | Booth et al. |

FOREIGN PATENT DOCUMENTS

| | | |
|---|---|---|
| WO | 2010/021879 A2 | 2/2010 |
| WO | 2010021879 A2 | 2/2010 |
| WO | 2015115397 A1 | 8/2015 |
| WO | 2015116371 A1 | 8/2015 |
| WO | 2015116401 A1 | 8/2015 |
| WO | 2017031440 A1 | 2/2017 |
| WO | 2017213933 A1 | 12/2017 |

OTHER PUBLICATIONS

Anonymous: "Insulin Pump," Wikipedia, Dec. 11, 2011.
Cobelli, et al., "Artificial Pancreas: Past, Present, Future," Diabetes, vol. 60, No. 11, Nov. 2011.
Office Action received for TW Appln No. 101148908 dated Jul. 21, 2014, pp. all.
First Office action dated Apr. 20, 2015 issued for Australian appln No. 2012358357, pp. all.
Office Action received for EP Appl. No. 12860239.8 dated Dec. 9, 2016, pp. all.
Supplementary Search Report dated Jun. 10, 2015 for EP Appln No. 12 860 239.8, pp. all.
"Insulin Pump", Wkipedia, Dec. 11, 2011, pp. all.
International Search Report for PCT/US12/71249 dated Apr. 12, 2013, pp. all.
Written Opinion for PCT/US12/71249, dated Apr. 12, 2013, pp. all.
Cobelli, Claudio et al., "Artificial Pancreas: Past, Present, Future", Diabetes, vol. 60, Nov. 2011, pp. all.
Hann, et al., "Intergral-based parameter identification for long-term dynamic verification of a glucose-insulin system model", Computer Methods and Programs in Biomedicine, Apr. 2005, pp. 259-270.
Lin, et al., "Stochastic modeling of insulin sensitivity variability in critical care", Biomedical Signal Processing and Control, 2005, pp. 229-242.

(56) References Cited

OTHER PUBLICATIONS

Nolte, et al., "Pancreatic Hormones & Antidiabetic Drugs", Katzung B. (ed) Basic and Clinical Pharmacology, Jan. 2004, pp. 711-734.
Secend Office Action received for EP Appiication No. 12860239.8, dated Jul. 30, 2018; pp. all.

* cited by examiner

——————— Start / Restart ———————
○ SubQTool calculates the starting dose (no insulin in past 24 hours or unknown)
○ Starting dose is based on current EndoTool data
○ Starting dose is based on IV Insulin data (not from EndoTool)
    Patient's Basis Glucose: [_____] mg/dL
    Patient's Drip Rate: [_____] units/hr ○ Starting dose is based on SubQ Insulin data (not from SubQTool)

Enter any SubQ insulin the patient has received in the past 24 hours.
(Enter 0 for Current Short-Acting and Long-Acting Insulin if none has been given.)

Current Short-Acting Insulin Total Daily Dose: [_____] units
(Do not include correction Insulin)
    Last Dose
    Time: [_____]
    Dose: [_____] units
    Type: [_____ ▾]

Current Long-Acting Insulin Total Daily Dose: [_____] units
    Last Dose
    Time: [_____]
    Dose: [_____] units
    Type: [_____ ▾]

[Save & Continue] [Close]

Meal Carbs

Search: [            ]  [Show All]

| Food | Carbs/Serving (gm) |
|---|---|
| Breakfast Cereals | |
| Shredded Wheat, 1 ounce (2/3 cup) | 22 |
| Oatmeal, 1 package | 30 |
| Fruits | |
| Apple, medium | 20 |
| Orange, medium | 20 |
| Banana, medium | 25 |
| Vegetables | |
| Broccoli, 1 stalk (1/2 cup) | 5 |
| Green beans, 1/2 cup | 7 |
| Carrot, medium | 10 |
| Peas, 1/2 cup | 10 |
| Corn, 1/2 cup | 18 |
| Bread-Type Foods | |
| Waffle, 1 Eggo | 17 |
| English Muffin, 1 | 25 |
| Bagel, average (3 ounces) | 45 |
| Submarine roll, 8 inch | 60 |
| Beverages | |
| Milk, 2%, 8 ounces | 13 |
| Orange juice, 8 ounces | 25 |
| Apple juice, 8 ounces | 30 |

[Close]

| Patient Demographics | Glucose and Nutrition | IV / TF / TPN | Confirmation | Order | Summary |

Squarepants, Spongebob

Birth Date: 12 Mar 1960 (50y)  MRNum: 1234567890123456789 0
Gender: Male  Room/Bed: 612
 Visit ID: 1234567890123456789 0

Insulin

| | Ordered | Delivered |
|---|---|---|
| Long-Acting Insulin Type: | None | None |
| Long-Acting Insulin: | | 0 units |
| Meal Coverage Insulin Type: | Novolog | None |
| Meal Coverage Insulin: | 4 units | 4 units |
| Correction Insulin Type: | Novolog | Regular |
| Correction Insulin: | 2 units | 2 units |

Treatment for Low Glucose

| | Ordered | Delivered |
|---|---|---|
| Carbs: | 80 gm | 80 gm |

Update values only if they are different from the ordered/estimated values.

Nutritional Carbs

| | Estimated | Actual | |
|---|---|---|---|
| Meal: | 20 gm | 20 gm | Carb Values |
| Supplement/Bolus Tube Feed: | 20 gm | 20 gm | Carb Values |
| Snack: | 20 gm | 20 gm | Carb Values |

Other

On Steroids: Yes ▾
Emesis occurred since last glucose: ☐

[ Confirm All & Continue ]   [ Close ]

FIG. 9I

| Patient Demographics | Glucose and Nutrition | IV / TF / TPN | Confirmation | Order | Summary |

Squarepants, Spongebob     Birth Date: 12 Mar 1960 (50y)    MRNum: 1234567890123456789
                                       Gender: Male                  Room/Bed: 612
                                                                                               Visit ID: 1234567890123456789

Glucose: 180 mg/dL
Glucose Timing: AC/HS and 03:00

Since the glucose was high, please check again in 2 hours.

Administer the following subcutaneously now:
- Long-Acting Insulin
  - Type: Lantus
  - Amount: 20 units

- Meal Coverage Insulin
  - Type: Novolog
  - Amount: 6 units    4 units scheduled
                             2 units for correction

- Correction Insulin
  - Type: Regular
  - Amount: 2 units

[Accept]

FIG. 9J

| Patient Demographics | Glucose and Nutrition | IV / TF / TPN | Confirmation | Order | Summary |

Squarepants, Spongebob

Birth Date: 12 Mar 1960 (50y)
Gender: Male

MRNum: 1234567890123456789
Room/Bed: 612
Visit ID: 1234567890123456789

Glucose: 60 mg/dL
Glucose Timing: AC/HS and 03:00

Since the glucose was low, please check again in 15 minutes.

Recommended Carb Intake: 30 gm

Patient is conscious and able to swallow, administer now:
- 12 oz (1.5 cups) of orange juice OR
- 20 oz (2.5 cups) of milk OR
- 8 glucose tablets OR
- Equivalent Otherwise administer now:
- 50 mL D50W IV Push OR
- Equivalent

[ Accept ]

SYSTEMS AND METHODS FOR DETERMINING INSULIN THERAPY FOR A PATIENT

CROSS REFERENCE TO RELATED APPLICATION(S)

This application is a continuation of pending U.S. patent application Ser. No. 13/725,115 entitled "SYSTEMS AND METHODS FOR DETERMINING INSULIN THERAPY FOR A PATIENT," filed Dec. 21, 2012 and issued as U.S. Pat. No. 10,046,113 on Aug. 14, 2018, which application claims the benefit under 35 U.S.C. § 119(e) of the earlier filing date of U.S. Provisional Application 61/578,693 entitled "SYSTEMS AND METHODS FOR DETERMINING SUBCUTANEOUS INSULIN THERAPY FOR A PATIENT," filed Dec. 21, 2011. The aforementioned applications and patent are incorporated herein by reference, in their entirety, for any purpose.

TECHNICAL FIELD

Examples described herein include therapeutic decision support systems involving periodic delivery of medications to a patient to achieve a particular physiological objective. For example, examples described herein relate to systems and methods for determining insulin therapy for a patient. The insulin therapy may be subcutaneous, intravenous, or may be a combination of subcutaneous and intravenous therapies.

BACKGROUND

Treatment of hospitalized patients frequently involves control of one or more physiological parameters in concert with administration of fluids, pharmaceuticals, and nutrition. For patients diagnosed with diabetes, treatment generally includes monitoring blood glucose levels, and administering insulin or carbohydrates when the blood glucose levels are not within acceptable ranges.

A patient may be diagnosed with specific types of diabetes mellitus that differ in onset, therapy and underlying disease state. In the case of "type 1" diabetes, the patient is dependent upon administration of exogenous insulin on a daily basis either by subcutaneous injections or by delivery from an externally worn insulin pump. In a person with "type 2" diabetes, the patient may or may not be dependent on the administration of exogenous insulin subcutaneously. Type 2 patients may require oral medications to either stimulate their pancreas to secrete insulin, or sensitize their tissues to the insulin provided by their pancreas. At times, type 2 patients may need additional insulin administered subcutaneously for them to remain in glycemic control. In a third type of diabetes, a "gestational" type, a female who exhibits normal glycemic control during non-gravid periods loses this control while pregnant (typically in the third trimester) and behaves somewhat like a type 2 diabetic. Persons with these three types of diabetes generally arrive at or are admitted into a hospital with known diabetes. In contrast, in a fourth type, "stress" diabetes, hyperglycemia occurs as a result of stress, illness or steroid administration, often just prior to or during a hospital stay and the patient requires therapeutic intervention through oral medications or by insulin administration. Studies have shown that proper glucose management during in-patient treatment reduces morbidity and mortality.

A goal in the treatment of any of the types of diabetic patients is to maintain blood glucose levels within an acceptable range, typically 80-120 mg/dL, 100-140 mg/dL or 100-180 mg/dL, using oral medications or through administration of insulin (subcutaneously or via a pump intravenously) while at the same time reducing the risk of hypoglycemia (glucose levels less than 70 mg/dL). Existing subcutaneous insulin dosing protocols may be limited in their goal to maintain glycemic control while accounting for patient-to-patient variability in insulin requirements as well as changes through time. Limitations may be related to the availability, management and utilization of information that would aid in an improved calculation of an insulin dose. However, access to useful information, entry of the useful information into some form of a calculation sheet, and calculating the dose based on the information would be a time consuming task for a nurse.

SUMMARY OF THE INVENTION

Within one aspect described herein, a method for determining a patient therapy is provided. An example method may include receiving information associated with a glucose measurement value of the patient, receiving information associated with anticipated nutrition intake for the patient, and receiving information indicating a short-acting insulin-on-board for the patient. The short-acting insulin-on-board may be associated with an amount of short-acting insulin that remains in the patient due to a prior insulin administration. The method may also include based, at least in part, on the information associated with the glucose measurement value of the patient, the anticipated nutrition intake for the patient and the short-acting insulin-on-board, determining at least one of a short-acting subcutaneous insulin dosage recommendation, an intravenous insulin dosage recommendation, a correction subcutaneous insulin dosage recommendation, a recommended amount of carbohydrates to be administered to the patient, or combinations thereof. The method may also include receiving information indicating a confirmation of a nutrition intake for the patient, and receiving information indicating a long-acting insulin-on-board for the patient. The long-acting insulin-on-board may be associated with an amount of long-acting insulin that remains in the patient due to a prior insulin administration. The method may also include based, at least in part, on the information associated with the long-acting insulin-on-board for the patient, the glucose measurement value of the patient, and the confirmation of the nutrition intake for the patient, determining a required long-acting subcutaneous or IV insulin dosage for the patient. The method may also include adjusting the short-acting subcutaneous insulin dosage or IV insulin dosage recommendation based, at least in part, on a difference between the long-acting insulin-on-board and the required long-acting subcutaneous or IV insulin dosage, and outputting an indication of at least one of the required long-acting subcutaneous insulin dosage, the adjusted short-acting subcutaneous or IV insulin dosage recommendation, the IV insulin dosage recommendation, the correction subcutaneous insulin dosage recommendation, the recommended amount of carbohydrates to be administered to the patient, or combinations thereof.

Any of the methods described herein may be provided in a form of instructions stored on a non-transitory, computer readable medium, that when executed by a computing device (e.g. a computing system), perform functions described. Embodiments may also include articles of manufacture including a tangible computer-readable media that have computer-readable instructions encoded thereon, and the instructions may comprise instructions to perform functions described herein.

In another aspect, a non-transitory computer readable medium having stored therein instructions executable by a computing device to cause the computing device to perform functions is provided. The functions may comprise providing a graphical user interface (GUI) to display information divided based on a category of input. The categories may include information associated with a glucose measurement value of a patient, associated with anticipated nutrition intake for the patient, indicating a short-acting insulin-on-board for the patient, indicating a confirmation of a nutrition intake for the patient, and indicating a long-acting insulin-on-board for the patient, for example. The functions may also include based, at least in part, on the information associated with the glucose measurement value of the patient, the anticipated nutrition intake for the patient and the short-acting insulin-on-board, determining at least one of a short-acting subcutaneous insulin dosage recommendation or a correction subcutaneous insulin dosage recommendation to be administered to the patient. The functions may also include based, at least in part, on the information associated with the long-acting insulin-on-board for the patient, the glucose measurement value of the patient, and the confirmation of the nutrition intake for the patient, determining a required long-acting subcutaneous insulin dosage for the patient, and adjusting the short-acting subcutaneous insulin dosage recommendation based on a difference between the long-acting insulin-on-board and the required long-acting subcutaneous insulin dosage. The functions may also include providing on the GUI a display of the required long-acting subcutaneous insulin dosage, the adjusted short-acting subcutaneous insulin dosage recommendation, and the correction subcutaneous insulin dosage recommendation to be administered to the patient.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

FIGS. 9A-9L illustrate example GUIs that may be implemented on a computing device to receive and display information according to embodiments disclosed herein.

DETAILED DESCRIPTION

In the following detailed description, reference is made to the accompanying figures, which form a part hereof. In the figures, similar symbols typically identify similar components, unless context dictates otherwise. Illustrative embodiments described in the detailed description, figures, and claims are not meant to be limiting. Other embodiments may be utilized, and other changes may be made, without departing from the scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

This disclosure may disclose, inter alia, systems and methods for determining subcutaneous insulin therapy for a patient. In one example, information associated with a glucose measurement value of the patient, anticipated nutrition intake for the patient, and a short-acting insulin-on-board for the patient can be received. Based, at least in part, on this information at least one of a short-acting subcutaneous insulin dosage recommendation, a correction subcutaneous insulin dosage recommendation, an intravenous insulin dosage recommendation, a recommended amount of carbohydrates to be administered to the patient, or combinations thereof can be determined. In addition, information indicating a confirmation of a nutrition intake for the patient, and a long-acting insulin-on-board for the patient can be received, and based, at least in part, on this information, a required long-acting subcutaneous or intravenous insulin dosage for the patient can be determined. The short-acting subcutaneous insulin dosage or intravenous insulin dosage recommendation can be adjusted based on a difference between the long-acting insulin-on-board and the required long-acting subcutaneous or intravenous insulin dosage. Other embodiments and examples are described herein.

In some examples, intravenous (IV) insulin dosing may be recommended and/or adjusted in a manner that accounts for insulin-on-board due in part to prior or simultaneous long- and/or short-acting subcutaneous insulin doses.

Figure 1:
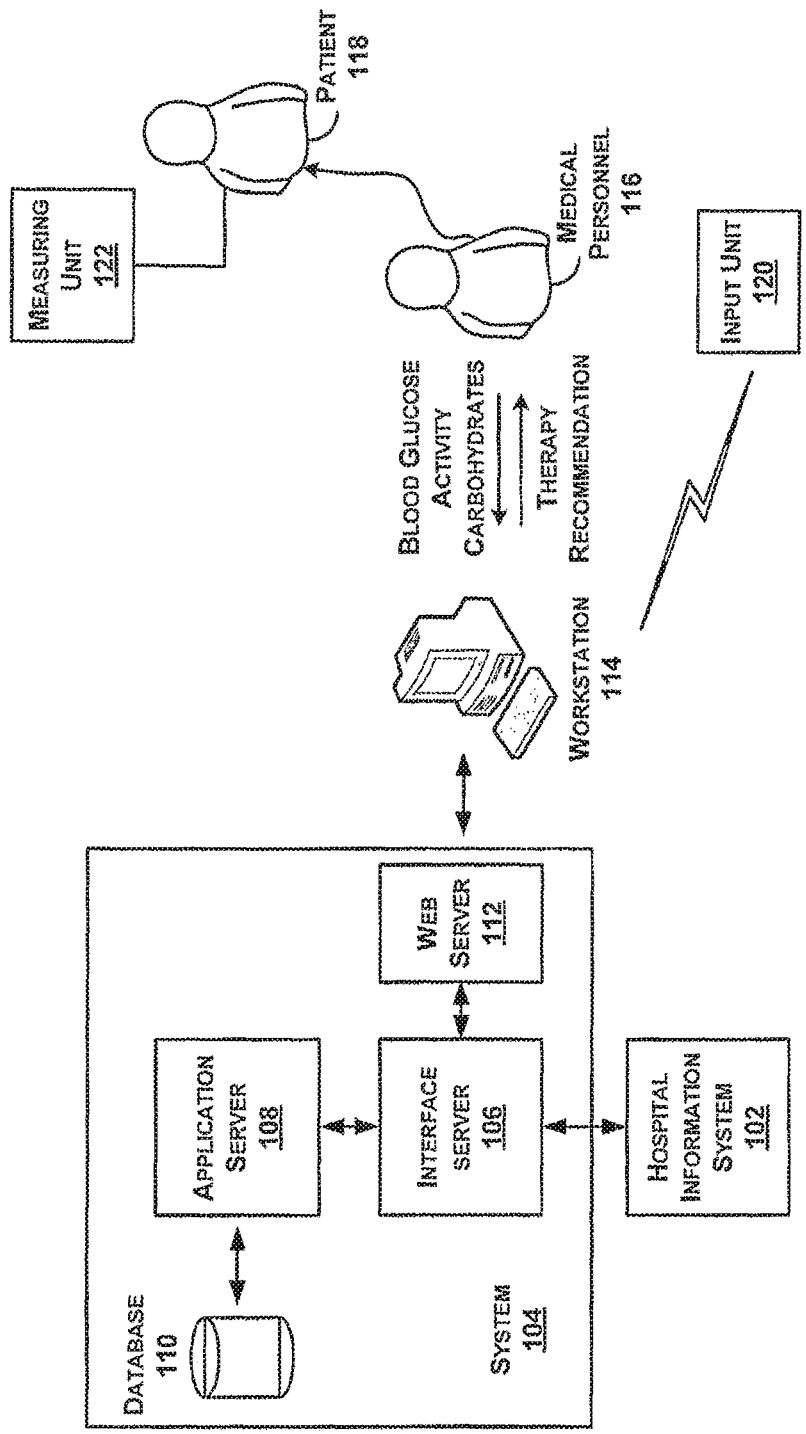
FIG. 1 illustrates an example system configuration for managing and delivering patient therapy.

Referring now to the figures, FIG. 1 illustrates an example configuration for managing and delivering patient therapy. A hospital information system 102 may be provided to support, for example, admission, discharge, and transfer of patient data throughout a hospital or medical community. The hospital information system 102 may be in the form of a server or other type of computing system (e.g. workstation), and may be connected to a computing system 104 via a network or other interface, such as for example, an interface server 106. Additionally, the hospital information system 102 and/or computing system 104 may include or be in communication with any of the laboratory, medication administration record, food services, vitals, pharmacy, and other information systems that may have information relevant to a patient and may broadcast information to other systems. The computing system 104 may include an application server 108 coupled to a database 110 that may include patient-specific information relating to treatment for the patient. The computing system 104 may also include a web server 112 enabling connections to the computing system 104 by other components using Internet, http, and messaging protocols over a local area network, wide-area network, or mobile network, wired or wireless.

The interface server 106 may also transmit data or messages through a common protocol, such as HL7, to the hospital information system 102. For example, orders determined by the applications described herein, glucose values and other patient specific information, which may be entered by clinicians as described herein, and confirmed meal and insulin dosing information, which may be entered by clinicians as described herein, may be transmitted to and from the hospital information system 102.

A workstation 114 may be connected to the system 104 for use by a hospital administrator, physician or nurse to input patient data, and to provide the ability to generate reports, receive patient status information, generate and print subcutaneous insulin dosing orders, and modify configuration parameters, for example. The workstation 114 may connect to the system 104 through the web server 112 or the interface server 106, or may connect directly to the application server 108, for example. The hospital information system 102, the system 104, and the workstation 114 may be located in a hospital or off-site as well.

The configuration in FIG. 1 may include additional components, such as other medical network servers connected to the system 104 to access and receive patient-specific data, critical care information, or other information useful for hospital personnel. Still further one or more of the described components or functions of the configuration in FIG. 1 may be divided up into additional functional or physical components, or combined into fewer functional or physical components. For example, the workstation 114 may alternatively be configured for autonomous operation without connection to a server or any of the hospital information system 102 or the system 104, for example. In some further examples, additional functional and/or physical components may be added to the examples illustrated by FIG. 1.

It is to be understood that examples of computing systems described herein may be quite flexible. In some examples, the application server 108 that may provide therapy recommendations based on received inputs as described herein, may be located at a hospital site. In some examples, the application server 108 may be integrated with the workstation 114 such that a same computing system used to input patient information may also be used to determine the therapy recommendation. In other examples, the application server 108 that may provide therapy recommendations may be located remotely, e.g. software described herein may be implemented as a cloud-based solution, where a server (e.g. the application server 108) may be programmed to provide therapy recommendations in accordance with examples described herein and communicate with local devices workstation 114) over a network, such as the Internet.

A user (e.g. a nurse or other medical personnel 116) may input data to the workstation 114 to receive information regarding therapy to deliver to a patient 118. In other examples, data may be input to the workstation 114 and/or provided to the system 104 in an automated manner, such as by transmission by a measuring unit that obtains one or more measured values regarding a patient's condition. A user (e.g. medical personnel 116) may input data to the workstation 114 directly, or the medical personnel 116 may use an input unit 120 that can communicate the data to the workstation 114 and/or to the system 104, such as to the application server 108, using a wireless or wired connection, for example. As one example, the input unit 120 may be a hand-held device such as a PDA, tablet, cellular phone, or mobile interface system.

A measuring unit 122 can be operatively connected to, associated with or used on the patient 118 to sense, monitor or measure a patient physiological characteristic or response to therapy. Blood or another fluid can be withdrawn from the patient and tested or analyzed by the measuring unit 122. For example, the measuring unit 122 may include a blood pressure monitor, temperature sensor, activity monitor, a blood-glucose monitor, or other monitor/meter as needed to measure a desired characteristic of the patient 118. For example, patients carrying the diagnoses of diabetes or hyperglycemia may have their blood tested periodically usually using a hand-held glucometer or in a continuous or semi-continuous manner through a continuous glucose measurement system (CGMS). The test can be performed by a nurse, nursing assistant or by a diabetic team. In some examples, the test may be performed in an automated (e.g. scheduled) manner. The test may be a "Finger Blood Glucose" test (FBG), and values obtained from these tests are in units of milligrams per deciliter (mg/dL) for United States hospitals and can range from 20-600 mg/dL. Meters outside the United States use units of millimoles per liter (mmol/L) and can range from 1.12-33.6 mmol/L, (conversion factor=0.056).

The glucometer readings can be entered into the workstation 114 by the medical personnel 116, or alternatively, the measuring unit 122 may provide the readings to the workstation 114 via a wireless or wired connection. Blood glucose tests may be performed on patients, four times a day on any one patient in one example. The tests can be performed before each meal and at bedtime, for example. Additional tests can be performed if before a meal there is an abnormally high glucose reading (>150-200 mg/dL) or an abnormally low glucose reading (<60 mg/dL). These additional tests can be performed in a time range of about 30-60 minutes after the abnormal reading or after an intervention in response to the original abnormal reading has been initiated (e.g., administration of insulin, administration of intravenous or oral glucose).

Alternately, blood glucose may be measured automatically by a device that is connected to the patient and analyzes a blood sample either continuously or regularly. The device may, for example, draw blood from a peripheral access point through an IV set, perform a glucose analysis via an in-line glucose-oxidase sensor and re-infuse the blood back into the patient automatically and without clinician intervention. In another arrangement, blood glucose may be measured by a continuous glucose monitor that is connected to the patient and may be based upon a sensor measurement in which the sensor is inserted into the patient's subcutaneous tissue layer.

Glucose measurements may be electronically transferred from the glucose measurement device to the application server or other computing system or computing system component through a number of arrangements. First, the clinician may manually enter the glucose value into the workstation or handheld device, which enables communication to the application and database systems. Second, the glucose measurement may be communicated directly from the glucose measurement device to the remote workstation or handheld device. Third, the glucose measurement may be electronically transferred from the glucose measurement device to the application through either a wireless, local area network or messaging system. Fourth, the glucose measurement may be collected and communicated either electronically or manually to the hospital laboratory information system. In this last arrangement, the glucose value associated with a particular patient is provided to the glucose management system through the Hospital Information System 102.

The medical personnel 116 may enter additional data into the workstation 114 including data indicating an activity level of the patient 118, an event or drug administration affecting blood glucose such as emesis or a change in steroid therapy, and data indicating an amount of carbohydrates consumed by the patient 118 or anticipated to be consumed by the patient 118. The workstation 114 may then provide a recommendation of therapy to the medical personnel 116, such as by displaying a recommendation on a display of the workstation 114 and/or input device or by printing a recommendation or providing the recommendation for display on another device associated with the care provider (e.g. a tablet PDA, or other mobile device). In addition, or alternatively, the workstation 114 may provide the recommendation of therapy to the input unit 120. The recommendation may indicate to administer to the patient a short-acting insulin dosage recommendation(s), a long-acting subcutaneous insulin dosage recommendation(s), a correction subcutaneous insulin dosage recommendation, an intravenous insulin dosage recommendation, or combinations thereof. The intravenous insulin dosage recommendation may represent either an overall intravenous insulin dosage recommendation, a correction to an existing intravenous insulin dosage recommendation, or combinations thereof. The recommendation may additionally or alternatively recommend an amount of carbohydrate to be given to the patient. The recommendation may in some examples recommend no action to be taken at this time for the patient. In addition to providing a recommended dosage for insulin, including for different types of insulin in some examples, the workstation 114 may provide a time for a next glucose measurement.

The medical personnel 116 may administer insulin to the patient 118 subcutaneously using a syringe, or using an infusion pump, for example. The insulin administration may be in accordance with the therapy recommendation provided, for example, by the application server 108 to the workstation 114 and/or input unit 120. In some examples, the insulin administration may be provided automatically, e.g. by an infusion pump or other device receiving the therapy recommendation provided by the application server 108 and/or workstation 114. An example infusion pump may be programmed with software, such as ENDOTOOL™, where the software may include instructions for calculating appropriate insulin doses/rates and glucose measurement intervals to provide intensive insulin therapy. The software may provide clinicians with insulin dosage, DSOW dosage (Dextrose 50% in water) or other carbohydrate amount, and testing frequency (time of next glucose test) recommendations through a pump interface, for example. After the clinician has confirmed or modified the recommended insulin infusion rate, the pump infusion rate can be automatically changed.

When a patient is placed on a subcutaneous insulin regimen, a calculation that may be performed, e.g. by the insulin pump or by the application server 108, is that of determining a total daily dose of insulin that the patient will receive. For type 1 diabetics, about 0.1-0.3 units/kg of insulin may be required. For type 2 diabetics, about 0.4-1.0 units/kg of insulin may be required. Half of these amounts may be given subcutaneously as a long-acting insulin (e.g., detemir, glargine) before bedtime. The other half of these amounts may be distributed equally among three doses of fast-acting insulin (e.g., aspart, lispro) given subcutaneously 15 minutes before each meal, for example. Ii the patient is already taking insulin, the patient may be kept on the same home routine, or placed on a four-dose a day regimen using the total daily dose estimates. Glucometer readings guide any additional insulin that is added to the preprandial (before meal) doses of insulin. In the event of hypoglycemia, insulin doses may be withheld and some type of glucose containing product may be given to the patient either orally or intravenously until subsequent glucometer readings are above a physician's ordered level, for example. The above calculations and insulin administration may be generalizations that work well for some patients.

A patient in some examples may be placed on an intravenous insulin regimen where the patient had received, either previously or simultaneously, one or more subcutaneous insulin doses. In that event, insulin-on-board calculations as described herein may be used to provide an intravenous insulin dosage recommendation that accounts for the insulin-on-board due to subcutaneous insulin therapy. In the event a subcutaneous insulin dose is provided during intravenous insulin therapy, insulin-on-board calculations as described herein may be used to provide an intravenous insulin dosage recommendation that accounts for the insulin-on-board due to subcutaneous insulin therapy. The intravenous insulin dosage recommendation may be provided in the form of an adjustment to an existing intravenous insulin dosage recommendation.

The workstation 114 may be configured to provide a recommendation for therapy per patient based on a number of patient-specific inputs. The provided recommendation may utilize information received, for example, by the application server 108. Example inputs may include an amount of carbohydrates that the patient is likely to consume before an insulin dose, a timing and rate of any tube feedings, an amount of physical activity that the patient is/has performed, an administration of any dextrose-containing solutions, an administration of any steroid medications, an administration of any antibiotics, a lab value or biomarker related to renal and hepatic clearance, such as serum creatinine and albumin, any post-prandial emesis that occurred, subcutaneous insulin dose(s) received, and combinations thereof. Provision of any of these items and/or combinations of these items may influence a calculation of an insulin dose made by the workstation 114, web server 112 and/or the application server 108.

As an example, the workstation 114, web server 112 and/or the application server 108 may execute a software program associated with the software program EndoTool™, to calculate insulin dosing based on past glucose measurements. EndoTool may be used in intensive care units, for example, to assist a nursing staff in calculations of insulin dosing for patients that require glycemic control. The workstation 114, web server 112 and/or the application server 108 may execute an additional software program as a step-down tool from EndoTool to allow the nursing staff to calculate subcutaneous and/or intravenous insulin dosing based on past glucose measurements, for example.

The workstation 114 may be a general computer or computing device that executes the software program as an application program on the workstation 114. Alternatively, the workstation 114 may access the application program through the web server 112, and thus, the application program may be a web-based program located on a server (e.g. the application server or web server) and executed through a client browser program on the workstation 114.

Figure 2:
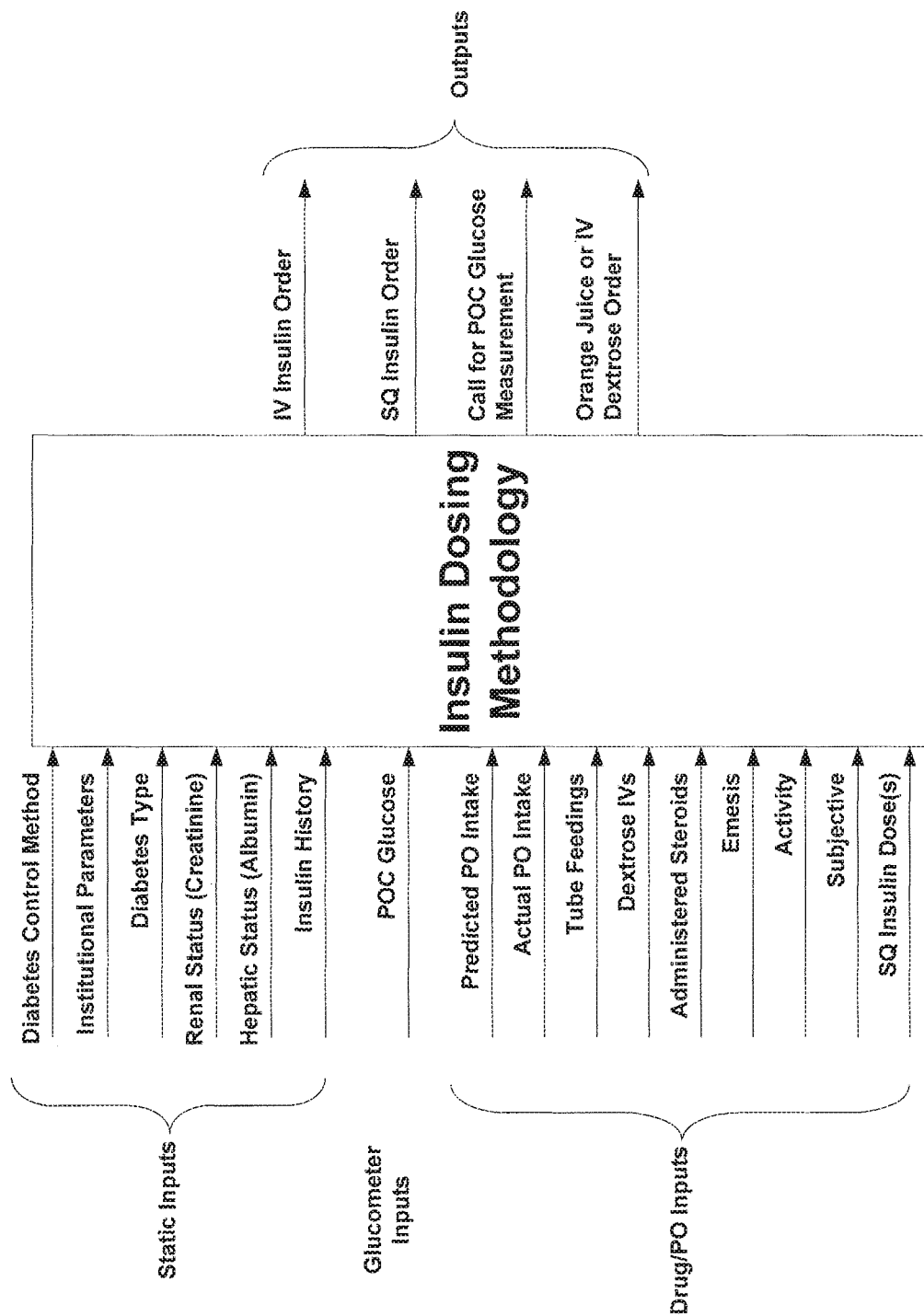
FIG. 2 is a block diagram of an example insulin dosing methodology showing inputs and outputs.

FIG. 2 is a block diagram showing inputs and outputs of an example insulin dosing methodology. The insulin dosing methodology may be implemented by the workstation 114 or the system 104 (or components of the system 104, e.g. the application server or web server) in FIG. 1, for example, to determine insulin dosage recommendations for administration to the patient. Accordingly, the workstation and/or the system 104 (e.g. the application server or web server) may be programmed to implement examples of the insulin dosing methodology described herein. For example, the workstation and/or the application server of FIG. 1 may include or be in communication with one or more computer readable mediums encoded with instructions that, when executed, cause the application server and/or the workstation to perform the actions for providing an insulin dosage recommendation described herein. The method may utilize three types of inputs, for example, that can be input per patient by a nurse or other user to a workstation and/or input device as described above. For example, static inputs, glucometer inputs, and/or drug (per oral (PO)) inputs may be used. Static inputs may include, but are not limited to, information indicating a diabetes control method used by the patient, any institutional parameters specific to the hospital, a diabetes type of the patient, a renal status (creatinine levels) of the patient, a hepatic status (albumin levels) of the patient, and any other information associated with an insulin history of the patient. Glucometer inputs may include, but are not limited to, blood glucose values (point-of-care (POC) glucose readings) obtained from glucometers used by the patients. Drug/PO inputs may include, but are not limited to, any predicted or actual enteral or parenteral carbohydrates taken in by the patient (e.g. including tube feedings), information associated with any dextrose intravenous (IV) drugs administered to the patient, information associated with any steroids administered to the patient, information indicating anticipated or actual activity levels of the patient, information indicating any emesis by the patient, information regarding previous or simultaneous subcutaneous insulin dose(s), and any other subjective information regarding activity of the patient.

The insulin dosing methodology may output a subcutaneous or intravenous insulin order to be administered to the patient. The subcutaneous insulin order may be an order to administer a short-acting insulin dosage, a long-acting insulin dosage, a correction insulin dosage, or combinations thereof, for example. The intravenous insulin order may specify a bolus and drip rate of IV insulin. The insulin dosing methodology may also or instead output a call for a POC glucose measurement to request an updated glucose reading. The insulin dosing methodology may further output an order to administer a carbohydrate containing solution to the patient (e.g., orange juice), for example, if the patient becomes hypoglycemic.

The insulin dosing methodology may calculate subcutaneous and/or intravenous doses of insulin that are to be administered to a patient to maintain a glycemic range of control, such as for example, between 80-120 mg/dL, of glucose in the bloodstream of the patient. The glycemic range of control may be adjusted, per patient, as set by a physician or hospital administrator.

The insulin dosing methodology may provide other outputs including but not limited to a graphical visualization of past glucose values, medical record reports of the blood glucoses, discharge summaries containing discharge instructions for the patient and the primary care provider, and quality assurance reports as required by an institution, for example.

The insulin dosing methodology may operate based on a proactive system of glucose control to predict preprandial and basal insulin doses based on glucometer readings preprandially, and on the history of glucometer readings as well as previous insulin doses and other status of the patient (e.g., steroid administration, oral intake), rather than based on a reactive system of glucose control where insulin doses may be only dependent upon the glucometer reading prior to a preprandial insulin dose.

The workstation 114, web server 112 and/or application server or system 104 may execute the insulin dosing methodology to provide a number of glucose control methods. Example glucose control methods include, but are not limited to, intravenous insulin, a single bedtime dose of long-acting insulin and three preprandial doses of short-acting insulin, a single bedtime dose of long-acting insulin and two preprandial doses of short-acting insulin, a single bedtime dose of long-acting insulin and one dinner dose of short-acting insulin, breakfast and dinner doses of insulin mixtures (e.g., Neutral Protamine Hagedorn (NPH)/Regular-70/30), and a single bedtime dose of long-acting insulin.

Figure 3:
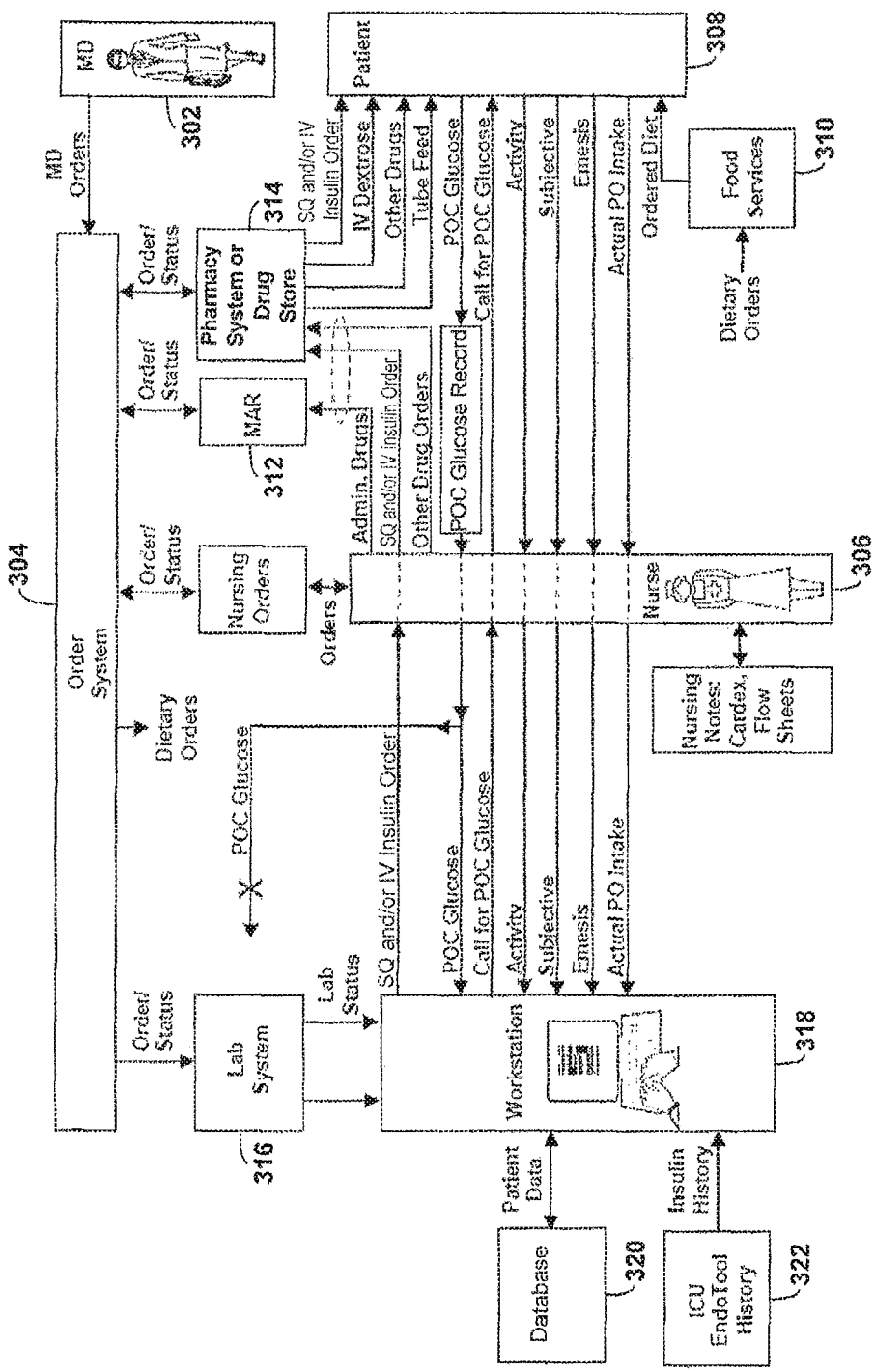
FIG. 3 illustrates another example system configuration for managing and delivering patient therapy.

FIG. 3 illustrates another example configuration for managing and delivering patient therapy. The configuration may be in the setting of a hospital, for example. Initially, orders to initiate a drug therapy may originate from a physician (MD) 302 using, for example, an electronic order system 304 (or alternatively, a paper-based order system). The order may include all or selected combinations of the following component orders as part of the order: 1) patient identification, 2) diabetic status of patient: type 1, type 2, hyperglycemic, or gestational, 3) a method of glycemic control to be used (e.g., use of a long-acting insulin in the evening and short-acting insulin before each of the three major meals, use of intravenous insulin, and/or glucometer readings to be performed before each meal and at bedtime), 4) changes to the diet, 5) a hypoglycemia protocol to use, and 6) required patient health status information (e.g., including creatinine, mass and other laboratory values).

The order system 304 may be configured to disseminate orders to various locations in the hospital that act on these orders. One of these locations may be a nurse 306 (or nurse station) assigned to a target patient 308. Methods of disseminating nursing orders include paper orders via patient charts and electronic orders via a workstation 114 or hospital information system 102, for example. Orders that define diet and food intake of the patient 308 may be disseminated to a food services department 310 (e.g., via paper, electronic transmission 106 or electronic orders to a workstation) and may not be intervened or controlled by nursing staff. Food for the patient 308 can be delivered to the patient 308 at specified times during the day and records can be kept by food services or the nursing staff as to what was actually delivered or consumed.

A medication administration record (MAR) system 312 may be coupled to the order system 304 to inform the order system 304 of drugs administered to the patient 308. The MAR 312 may provide drug administration orders that define a drug type, amount and timing of a drug to administer to the patient 308. The MAR 312 may be configured to generate drug orders from information received from the order system 304.

The order system 304 may also couple to a drug storage facility 314 to link drug orders to the order system 304 and to cause nursing staff to interact with the drug storage facility 314 to obtain a drug (or other treatment) for administration to the target patient 308. When items/drugs are removed from the drug storage facility 314, the order, pharmacy or billing systems can be notified of this removal. Alternatively, if a drug is not located in the drug storage facility 314 (e.g., insulin for patients may be part of a common drug storage facility located at a nursing station or other storage area), the MAR 312 can be updated with a dosage of any drug removed from the other areas and administered to the patient 308.

A lab system 316 may also receive orders from the order system 304 including instructions to perform blood draws and process these draws in the hospital's clinical laboratory, for example. Other orders to the lab system 316 may include orders involving studies to be performed on the target patient 308 such as radiologic, nuclear medicine or other procedure-like studies, for example. The lab system 316 processes orders with posting of laboratory results to the lab system 316 when available for future review/interpretation by healthcare personnel. This data could be available to the nursing staff at a workstation 318, and may include data relating to creatinine levels and point of care (POC) glucometer values, for example. Alternatively, the nurse 306 may enter the POC glucometer values manually into the workstation 318.

The patient 308 may receive a drug administered as directed by the order system 304. For example, the patient 308 may receive intravenous insulin, and/or may receive subcutaneous insulin administered by the nurse 306 once a day, four times a day, or other amounts. Additional doses of short-acting insulin may be given to the patient 308 dependent upon glucometer readings that dictate a need for additional doses based on a "sliding-scale" of insulin that the physician has ordered. In the event of hypoglycemia (blood glucose <60 mg/dL), the patient 308 may receive oral orange juice, oral glucose tablets or intravenous dextrose.

The patient 308 may be tested for their glucose levels using glucometers, and the nurse 306 can enter a glucometer reading into the workstation 318. In addition, the nurse 306 may enter activity levels and subjective information about the patient 308 into the workstation 318 that can be used to modify insulin dosing. As an example, the nurse 306 may measure activity levels of the patient 308 using a "pedometer-type" of device.

The workstation 318 may issue orders to administer insulin to the patient 308 depending upon a type of glycemic control methodology ordered by the physician 302 and allowed by the medical administrator of the floor/unit. After administration of subcutaneous insulin to the patient 308, the nurse 306 may enter a record of administration both into the MAR 312 and into the workstation 318.

The workstation 318 may receive glucose values/measurement times periodically from glucometer readings from the patient as well as quantity and times of predicted oral intake and/or actual intake as entered by the nurse 306, for example. Any tube feedings, emesis, quantity and type of activity performed by the patient, and any other drugs administered to the patient including steroids or dextrose containing solutions can also be entered into the workstation 318. The workstation 318 may use any of this information to determine future insulin doses and glucometer testing times, e.g. by executing a program for determining insulin doses in accordance with methodologies described herein.

The workstation 318 may interact with a database (e.g. a structured query language (SQL) database located on a SQL server database 320). The database may contain records of patients and their history. In the event that the patient 308 might have recently been cared for in the intensive care unit (ICU) using a system (e.g. the ENDOTOOL system) 322 for intravenous glycemic control, then underlying adaptive control parameters from this system 322 can be provided to the workstation 318 and used as a starting point for glycemic control. Such control parameters may characterize the patient's quantity of insulin used per day and insulin sensitivity. See co-pending U.S. Ser. No. 12/970,777 filed Dec. 16, 2010, which is incorporated by reference herein in its entirety, for additional information regarding the EndoTool system and transfer of control parameters for glucose control.

As an example, if the patient is "nothing by mouth" (NPO), an insulin dosing calculation may take the form of:

$I_t = f(t, g_t, \tilde{I}_{t-1}, \overline{\theta}_t, \overline{G})$ where t is the time, $I_t$ is a calculated regular (short-acting) insulin dose at time t, $\tilde{I}_{t-1}$ is a delivered insulin dose over the previous time period, $g_t$ is a glucose measurement at time t, $\overline{\theta}_t$ is a vector of calculated underlying patient-specific control parameters, $\overline{G}$ is a set of target glucose concentrations, and $f$ is a function that maps or translates the parameters into a recommended insulin dose. The parameter vector $\overline{\theta}_t$ may be referred to as underlying patient-specific control variables or parameters. The control parameters may enable determination of a patient specific insulin dose because the control parameters are calculated on the basis of an observed glucose response to insulin dosing. Additional inputs may be used including, but not limited to, prior glucose values, patient carbohydrate intake, changes in medications, such as steroids, exercise and patient specific conditions or states, or combinations thereof. Workstations or computing systems described herein may be programmed (e.g. using computer readable media encoded with executable instructions) to perform the insulin dosing methodologies described herein.

In some examples, the function $f$ above can be defined and the calculation of $I_t$ can be performed on the basis of the following nonlinear equation: $I_t = M_1(g_t - G) + M_2(g_t - G)^2$ where $I_t$ is greater than zero, $g_t$ is a glucose measurement, and $M_1, M_2 \in \overline{\theta}_t$ are multiplication constants estimated over time on the basis of error between an observed and desired glucose response to insulin dosing. The insulin dosing calculation is nonlinear because, for example, it includes a square term $(g_t - G)^2$. Accordingly, the calculation of $I_t$ may not linearly depend on the difference between the measured glucose and target glucose levels. Rather, a more complex, nonlinear relationship may be specified that may result in some examples in a more accurate representation of the recommended insulin dose. The method of calculating the underlying patient-specific control variables can be performed using a recursive least squares estimator, a Kalman filter, a Bayes estimator, or control rules based upon a level and change of patient glucose concentration over time, for example.

As an example, the method of calculating the underlying patient-specific control variables can be performed using established methods of parameter estimation, such as extended Kalman filtering, recursive least squares estimation, Bayesian estimation, or proportional control rules that are used to adjust $M_1$ and $M_2$ on the basis of a calculated error, such as a difference between observed and expected glucose concentrations. For example, see Goodwin and Sin, *Adaptive Filtering; Prediction and Control*, 1984, the entire contents of which are incorporated herein by reference.

As a specific illustrative example, under the assumption that the partial derivative of an observed glucose concentration with respect to a calculated insulin rate is negative (e.g., glucose levels decreases with increased insulin), a pseudo gradient descent methodology may be used to determine $M_1$ and $M_2$ on the basis of a difference between observed and desired glucose readings. For example, given the error: $e_t = \bar{g}_t - g_t$, where $\bar{g}_t$ is a desired or target glucose concentration at time t, the parameters $M_1$ and $M_2$ can be updated according to the following:

$$M_1 = M_1 - \alpha \cdot e_t$$

$$M_2 = M_2 - \beta \cdot e_t$$

where α and β are tunable positive constants. At each measurement, estimated underlying control variables may be updated according to non-linear equation $(I_t - M_1(g_t - G) + M_2(g_t - G)^2)$ and, in time, become personalized to the insulin-glucose response of the patient. These underlying control variables can be provided to the workstation 318 and used as a starting point for glycemic control, for example, in instances in which a patient has been cared for using such glucose dosing methodologies. Workstations and/or computing systems described herein may be programmed (e.g. using one or more computer readable media encoded with appropriate executable instructions) to calculate the underlying control variables and insulin dosing.

In some examples, $I_t$ may be determined through a feedback control methodology, such as proportional integral control (PID) or model predictive control.

Referring again to FIG. 1, the workstation 114 may determine and recommend a dose of each insulin administration after receiving information regarding prior insulin delivery, glucose measurements and/or expected carbohydrate consumption, for example. Any number of calculations may be used to determine long and short-acting subcutaneous insulin doses (injections) and/or intravenous insulin doses.

General or personalized insulin dosing recommendations and regimes may be used to treat a patient with diabetes.

As an example, if a patient is eating, an insulin and carbohydrate dose administration may be calculated, e.g. by the workstation 114 and/or by the system 104, such as by the application server 108) based upon the patient's daily basal insulin requirements, carbohydrate to insulin ratio (CIR in servings per unit of insulin) and/or pre-prandial glucose measurement. First, the computing system may recommend that the patient receive a basal insulin dose either one or two times per day of long or intermediate acting insulin (e.g., glargine, detemir or NPH). The dose may be recommended to be divided and distributed equally in the case of twice daily administration. Prior to each meal, a pre-prandial meal-dose of short-acting insulin may be determined, e.g. by the workstation 114 and/or by the system 104, such as by the application server 108) by dividing the expected carbohydrate intake by CIR and rounding down to the nearest unit. Based upon the patient's glucose level, a correction dose of short-acting insulin may also be recommended. The dose may be determined according to a correction scale as 1-4 units of insulin for every 50 mg/dL the patient's glucose level is above 150 mg/dL. The correction dose may be combined with the meal dose. In some examples, an intravenous insulin dosage recommendation may be provided that may, for example, specify a bolus size and drip rate for IV insulin therapy.

The basal rate, CIR and correction scale may be adjusted, e.g. as recommended by the workstation 114 and/or by the system 104, such as by the application server 108, every other day or as frequently as eight times per day based upon the patient's response to prior insulin administration. Two times per day may be used in one example. For example, if the patient's fasting glucose measurements and pre-prandial glucose measurements are received by the workstation 114 and/or the system 104, such as by the application server 108, and are recognized as consistently elevated, the recommended basal dose may be increased by a percentage (e.g., 10%). Alternately, a persistently low glucose value may lead to a decrease in the basal dose. In some examples, the nurse may increase or decrease the dose absent a recommendation from a computing system. The OR may be increased or decreased, e.g. in accordance with a recommendation by the workstation 114 and/or by the system 104, such as by the application server 108, based upon an additional patient's post-prandial glucose response. For example, if the patient's two hour post-meal glucose is over 200 mg/dL, as received by data communicated to the workstation 114 and/or the system 104, such as the application server 108, the CIR may be increased by 10%. Similarly, the correction scale may be increased or decreased by 1 unit on a daily basis if the patient's glucose is consistently high or low respectively.

The basal rate and CIR may be known based upon the patient's home insulin regimen. If the patient is newly diagnosed or experiencing stress induced hyperglycemia, the basal dose may be to 0.2-0.3 units/kg of total body weight. The CIR may be initially estimated as 15 grams of carbohydrate per unit of insulin and increased or decreased by the physician depending upon the patient's age, body size, activity level, steroid usage and insulin resistance.

As a second example, the general dosing recommendations may include a single injection of long-acting (e.g., basal) insulin in either the evening or morning and an injection of short-acting insulin prior to each meal. As an example, an order may be issued for administration of a basal dose of insulin at approximately 9 PM every evening for control methods that utilize this type of insulin. The insulin that may be administered can include NPH (e.g., Novolin N or Humulin N), Insulin detemir (e.g., Levemir), and Insulin glargine (e.g., Lantus), for example. The dose can be calculated, e.g. by the workstation 114 and/or system 104, such as the application server 108 of FIG. 1) as follows:

Basal *qPM* Insulin Dose=0.5*TDD where TDD is the total daily dose in units of any type of insulin given to the patient in one day. The remaining portion of the total daily dose of insulin may be equally distributed among three short-acting insulin injections prior to each meal.

In another general example, a method for calculating a subcutaneous dose of short-acting preprandial insulins is provided. For example, an order may be issued for the administration of a dose of insulin prior to each meal. The insulin that can be administered may include insulin aspart (e.g., Novolog), insulin glulisine Apidra), insulin lispro (e.g., Humulog), regular (e.g., Novolin R), and regular (e.g., Humulin R), for example. The dose may be calculated (e.g. by the workstation 114 and/or the system 104, such as the application server 108 of FIG. 1) as follows:

Preprandial Insulin Dose=Expected Carbohydrate Intake (grams or servings)/CIR and a correction dose as Correction Dose=$\beta(f[BG_t - \text{target}])$ where f is related to the patient's insulin resistance derived from the basal rate (Units/mg/dL), target is an upper glucose limit, BGi is the measured glucose concentration, and β is a multiplier (e.g., 0.4) that may be varied depending upon the patient's type of diabetes and kidney and hepatic clearance rates, (Units/(mg/dL)2

In still another general example, a method for calculating a subcutaneous dose of 70/30, 75/25 and 50/50 insulin mixtures is provided (e.g. the workstation 114 and/or system 104 such as the application server 108 of FIG. 1 may be programmed to calculate the subcutaneous dose). For example, an order may be issued for administration of bi-daily doses of insulin mixtures. The insulin that can be administered may include insulin aspart protamine suspension/aspart (e.g., Novolog Mix 70/30), insulin lispro protamine suspension/insulin lispro (e.g., Humulog Mix 75/25), insulin lispro protamine suspension/insulin lispro (e.g., Humulog Mix 50/50), NPH/Regular (e.g., Humulin 70/30), NPH/Regular Humulin 50/50), and NPH/Regular (e.g., Novolin 70/30).

In one embodiment, any of the general examples of insulin dosing regimes provided above may be personalized per patient. A set of methodologies may be provided (e.g. the workstation and/or computing systems described herein may be programmed to implement the described methodologies) to personalize recommendations to each individual patient by adapting a set of internal control parameters on the basis of patient variables (e.g., diabetes status, steroid use, etc.), observed nutritional intake and observed blood glucose response to insulin injections. Initialization of the control parameters can be made patient specific by considering age, weight, height, diabetes status, glomerular filtration rate (GFR) (via serum creatinine level) and prior insulin(s), for example. Adaptive control parameters may be used including a total daily dose of insulin, a nonlinear physiological dosing coefficient, and the ratio of long and short acting insulins. Updates to each parameter can be made on the basis of the nurse-entered information.

Example methodologies may further utilize GFR corrected insulin effect curves to account for insulin-on-board in order to reduce "stacking" of frequent short-acting insulin administrations that accumulate in the interstitium and to adjust for changes in the estimated total daily dose. Insulin-on-board refers to insulin that remains in the blood stream following prior insulin administrations. A distribution of insulin-on-board depends on the pharmacokinetics of the drug as well as the physiology of an individual. The effect of the insulin on board related to patient glucose management can be considered as part of an insulin dosing regimen.

A volume of all insulin in a person that will be active over a period of time (e.g., next five hours in one example) may be referred to as insulin-on-board. Thus, insulin-on-board includes previous insulin doses administered (over a previous $T_{max}$ hours), and may additionally include recommended insulin doses that may affect insulin activity during the period of time. In one embodiment, an amount of insulin-on-board in a patient can be determined, e.g. by the workstation 114 and/or system 104 of FIG. 1, such as by the application server 108 or web server, and may be used to determine amounts of short-acting or long-acting insulin requirements, or intravenous insulin, to be administered to a patient. For example, insulin requirements may be calculated using estimated internal control parameters including the patients total daily dose (TDD) or basal dose, and an adjustment to a current insulin recommendation (associated with meals or correction scale) may be made to compensate for insulin-on-board. The adjustment dose can be negative or positive and may have one of many effects. Adjustments can be made utilizing GFR adjusted insulin effect curves to provide appropriate action when the patient suffers from renal insufficiency, for example.

Adjustments to a calculated required amount of short-acting, long-acting, or intravenous insulin dosages can be made to adjust for changes associated with increased or decreased insulin sensitivity following delivery of a long-acting dose of insulin, changes associated with a change in diet following delivery of a long-acting dose of insulin, changes associated with an insulin therapy provided to the patient, changes due to non-uniformity in the shape of the insulin effect curve associated with long-acting insulin, changes due to residual insulin-on-board as a result of renal or hepatic insufficiency, and changes due to the correction scale portion of the short-acting insulin dose from frequent glucose measurements or snacks that precede a meal, for example. In addition, if a negative adjustment exceeds a recommended short-acting dose then a quantity of carbohydrates can be recommended for consumption/injection, for example.

Example adjustment scenarios are described below in Table 1. The examples indicate how a computing system (e.g. workstation 114 of FIG. 1, system 104, and/or application server 108 or web server) may alter a recommendation base don inputs received regarding patient status.

TABLE 1

1. When the patient's estimated insulin-requirements drop following a prior delivery of long-acting insulin, a negative adjustment dose is used to reduce the short-acting insulin dose to account for the previously administered long-acting insulin that had been administered on the higher TDD (or basal dose) schedule.
2. In the setting of an increased TDD associated with long-acting insulin or basal dose, a positive adjustment dose increases the short-acting insulin to account for a previously administered long-acting dose that was based on a smaller TDD.
3. In the setting of starting a patient without any long-acting insulin previously administered, a positive adjustment may be calculated increasing the short-acting insulin to account for the basal requirements prior to the long-acting insulin dose administration
4. In the setting of acute control situations for high blood glucose levels that dictate more frequent blood glucose checks, the adjustment dose may reduce the correction scale insulin in the setting of adequate blood glucose changes and in the setting of frequent short-acting insulin doses. This may have the effect of un-stacking the frequently dosed insulin to avoid hypoglycemia.
5. In the setting of an insulin regime change, an adjustment can be made to correct the dosing from the effects of previous regimes while transitioning to a new regime.
6. In the setting of frequent short-acting insulin doses (e.g., a snack followed by a meal), an adjustment can be made to account for the insulin-on-board and adjust the correction dose.
7. In consideration of the non-uniform action of long-acting insulin, an adjustment dose may compensate for periods of low or high insulin release.

Figure 4:
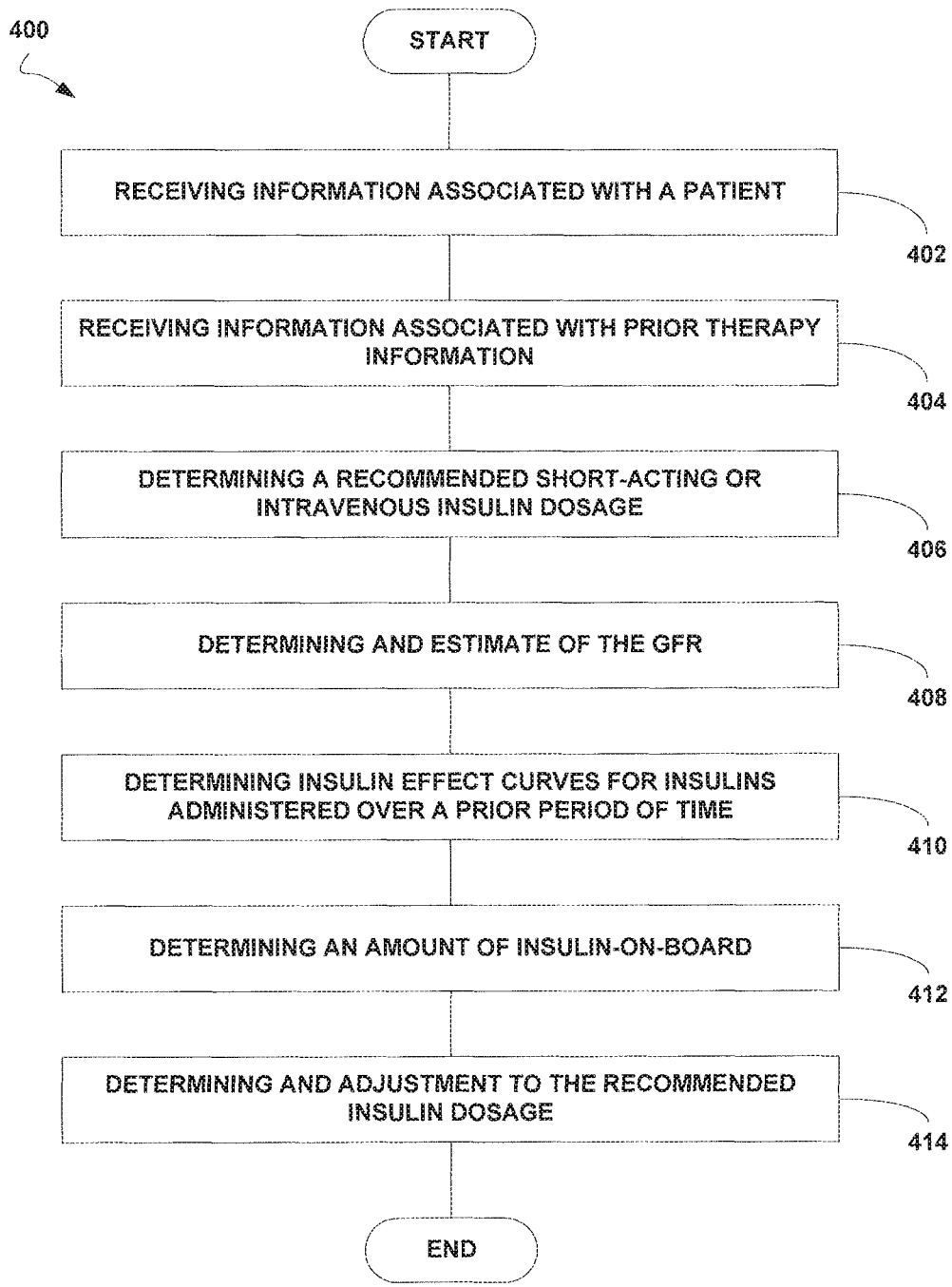
FIG. 4 is a block diagram of an example method to determine an adjustment to an insulin recommendation based on an amount of insulin-on-board, in accordance with at least some embodiments described herein.

FIG. 4 is a block diagram of an example method to determine an adjustment to an insulin recommendation based on an amount of insulin-on-board, in accordance with at least some embodiments described herein. Method 400 shown in FIG. 4 presents an embodiment of a method that, for example, could be used with the configuration shown in FIG. 1, and may be performed by the system 104 (e.g. by the application server 108 or web server), the workstation 114, or a combination of the system 104 and the workstation 114. Method 400 may include one or more operations, functions, or actions as illustrated by one or more of blocks 402-414. The method may be implemented by programming one or more of the computing systems (e.g. workstations and/or servers) of FIG. 1 to perform the operations, functions, or actions illustrated. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 400, and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard chive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, or compact-disc read only memory (CD-ROM), for example. The computer readable media may also be any other volatile or non-volatile storage systems. The computer readable medium may be considered a computer readable storage medium, for example, a tangible storage device, or other article of manufacture.

In addition, for the method 400, and other processes and methods disclosed herein, each block in FIG. 4 may represent circuitry that is wired to perform the specific logical functions in the block.

Initially, at block 402, the method 400 includes receiving information associated with a patient. For example, patient data may be received including, but not limited to, levels of serum creatinine, a diabetes type, an age, weight, and gender of the patient for example. Any combination of patient data may generally be received at block 402. The method 400 also includes, at block 404, receiving information associated with prior therapy information. For example, a type of insulin previously administered as well as amounts previously administered and times of previous administrations can be identified. The method 400 also includes, at block 406, determining a recommended short-acting insulin dosage or an intravenous insulin dosage. For example, the short-acting insulin dosage can be determined based upon the patient's current condition (e.g., current blood glucose levels) and expected carbohydrate intake using known insulin effect curves. The insulin effect curves may be stored as data accessible to the computing system implementing block 406. The data representing the insulin effect curves may generally be stored in any suitable electronic storage medium in communication with the relevant computing system, which storage medium may be the same or a different storage medium than the medium storing instructions to perform the sort-acting insulin dosage calculation.

At block 408, the method 400 may optionally include determining an estimate of the patient's GFR. Estimated GFR may include a measure of kidney function in medicine. Kidney filtration has an effect on insulin elimination from the body. A half-life of insulin may be increased by roughly two fold with a loss of kidney function (e.g., decreased GFR of ≤10 mL/min/1.73 m2). An example equation to determine an estimated GFR is provided below that provides a relationship between serum creatinine, gender, age, and ethnicity.

$$GFR = 141 \times \min\left(1, \frac{SCr}{\kappa}\right)^{\alpha} \times \max\left(1, \frac{SCr}{\kappa}\right)^{-1.209} \times 0.993^{age} \times F_{gender} \times F_{ethnicity}$$

where $$\kappa = \begin{cases} 0.9 & \text{gender} = \text{male} \\ 0.7 & \text{gender} = \text{female} \end{cases},$$

$$\alpha = \begin{cases} -0.411 & \text{gender} = \text{male} \\ -0.329 & \text{gender} = \text{female} \end{cases},$$

$$F_{gender} = \begin{cases} 1 & \text{gender} = \text{male} \\ 1.018 & \text{gender} = \text{female} \end{cases},$$

$$F_{ethnicity} = \begin{cases} 1.159 & \text{ethnicity} = \text{african american} \\ 1 & \text{otherwise} \end{cases}, \text{ and}$$

$$SCr = \begin{cases} SCr_{default,child} & (SCr = NULL) \wedge (age < 21) \\ SCr_{default,adult} & (SCr = NULL) \\ SCr_{max} & SCr > SCr_{max} \\ SCr_{min} & SCr < SCr_{min} \\ SCr & \text{otherwise} \end{cases}$$

GFR amounts may be estimated using other methods as well, and in other examples different values of the constants described above also be used.

At block 410, the method 400 includes determining insulin effect curves for insulins administered over a prior period of time. For example, insulin effect curves can be determined or identified for insulin injected over the last 36 hours. Known insulin effect curves can be used based on types and amounts of insulins administered. At block 410, a computing system may select, for example, among a variety of stored insulin effect curves base don types and amounts of insulin administered. In other examples, an insulin effect curve and/or data representing an insulin effect curve may be calculated in block 410.

Insulin effect generally describes the action of insulin through time and its availability to act on the patient's blood glucose. Insulin effect curves may determine insulin effect for each insulin type based upon the patient's kidney clearance as represented in the calculated GFR. In addition, an area under an insulin effect curve may determine a volume, and/or a 75% and 95% utilization time (e.g., in hours) of the insulin. Initially, pharmaco-kinetic/dynamic (PK/PD) curves for each insulin type may be provided with a sampling constant interval through time equal to $T_S$ which may be nominally set to 15 minutes, for example. In the event that PK/PD curves are unknown, a short-acting insulin response may be approximated to be uniform over a five hour period and a long-acting insulin response may be approximated to be uniform over a 24 hour period.

For each type of insulin, the insulin effect $(R(\text{type}, j) \forall j=1, 2, K, N_R)$ may be a normalized vector that defines an expected serum insulin availability versus time taking into account the patient's GFR. In one example, insulin effect curves may be determined given the following:

TABLE 2

1. An estimate of the GFR
2. P recent insulin administration times, $ti_k$, where k: 1, 2, ..., P, $t_i - ti_k < T_{max}$ hours, and $t_i$ is a current time
3. Indices to a global insulin list specifying a type of long-acting and short-acting insulin administered at each administration event, $\text{LAtype}_k$ and $\text{SAtype}_k$, respectively, where k: 1, 2, ..., P refers to the administration event
4. Times associated with short-acting and long-acting insulin administration prior to patient enrollment and during a last $T_{max}$ hours ($ti_{SA, init}$ and $ti_{LA, init}$, respectively) and types of short-acting and long-acting insulin administered prior to patient enrollment ($\text{SAtype}_{init}$ and $\text{LAtype}_{init}$, respectively) where $t_i - ti_{LA, init} < T_{max}$ and $t_i - ti_{SA, init} < T_{max}$
5. A matrix of insulin actions for each insulin delivered, E(type, j), where (type) is an m-dimensional index to the unique insulin types (specified in $\text{LAtype}_k$, $\text{SAtype}_k$, $\text{SAtype}_{init}$ and $\text{LAtype}_{init}$) and j is the index of Ts-minute time intervals such that an example insulin response time is determined according to $t_R = (j - 1) \times Ts$ minutes
6. A number ($N_R$) of j elements in the insulin response matrix E(type, j), such that $N_R = T_{max} \times \dfrac{60}{Ts}$ To determine the insulin effect curves, the estimate of the GM can be bounded such as:

$$GFR_b = \begin{cases} GFR_{max} & GFR_i > GFR_{max} \\ GFR_{min} & GFR_i < GFR_{min} \\ GFR_i & \text{otherwise} \end{cases}$$

Next, a unique subset of M indices, type(m) where m: 1, 2, ..., M, of insulin type index variables $\text{LAtype}_k$, $\text{SAtype}_k$, $\text{SAtype}_{init}$ and $\text{LAtype}_{init}$ can be established.

Coefficients of a second order digital filter defining insulin effect from insulin PK curves can be specified. For example, using definitions of total plasma clearance term n=0.16, the portion or plasma clearance attributable to the kidney $r_k$=0.6, the sampling interval $T_S$=15 minutes and the time constant associated with the interstitial clearance T=36 minutes, the coefficients can be specified according to:

$$B = [1 \ 2 \ 1]$$

$$A = \begin{bmatrix} \left(k_1 + \dfrac{2}{Ts}\right)\left(k_2 + \dfrac{2}{Ts}\right) \\ 2k_1 k_2 - 2\left(\dfrac{2}{Ts}\right)^2 \\ \left(k_1 - \dfrac{2}{Ts}\right)\left(k_2 - \dfrac{2}{Ts}\right) \end{bmatrix}$$

where $$k_1 = \dfrac{-\ln(0.5)}{T}$$

$$k_2 = n \cdot \left(r_k \dfrac{GFR}{100} + (1 - r_k)\right),$$

and B and A correspond to coefficients of the numerator and denominator of a transfer function of the filter, respectively. Then, for each insulin type, (type(m)) where m: 1, 2, ..., M, the insulin effect can be calculated recursively according to a following form of the transfer function:

$$R(\text{type}, j) = \dfrac{1}{A(1)}(S2(j-1) + B(1) \cdot E(\text{type}, j))$$

-continued $$S2(j) = S3(j-1) + B(2) \cdot E(\text{type}, j) - A(2) \cdot R(\text{type}, j)$$

$$S3(j) = B(3) \cdot E(\text{type}, j) - A(3) \cdot R(\text{type}, j)$$

where j=1, 2, ..., NR, A(j) and B(j) correspond to the jth element of the vectors A and B, the states S2(0) and S3(0) are zero and (type) is used to denote (type(m)). After calculation, each insulin effect curve can be normalized to an area of one:

$$R(\text{type}, j) = \dfrac{R(\text{type}, j)}{Y} \forall j = 1, 2K \ N_R \text{ where } Y = \sum_{j=1}^{N_R} R(\text{type}, j).$$

Calculation of the 75% and 90% cut-off points for each insulin type may occur by determining $\text{insulin}_{75}(\text{type})$ and $\text{insulin}_{90}(\text{type})$ from the distribution curves of R(type,j). For example, $$\text{insulin}_{75}(\text{type}) = \dfrac{j_{75}}{60/Ts}$$

such that $$\sum_{j=1}^{j_{75}-1} R(\text{type}, j) < 0.75 \leq \sum_{j=1}^{j_{75}} R(\text{type}, j)$$

Similarly, $$\text{insulin}_{90}(\text{type}) = \dfrac{j_{90}}{60/Ts}$$

such that $$\sum_{j=1}^{j_{90}-1} R(\text{type}, j) < 0.90 \le \sum_{j=1}^{j_{90}} R(\text{type}, j).$$

In some examples, insulin on board due to a previously or simultaneously administered subcutaneous insulin dose may be calculated utilizing the insulin on board calculation methodologies described herein. The insulin volume ($I_{effect}$) may be determined by summing an area under the insulin curve, which may be for example calculated as follows:

$$I_{effect} = Idose \sum_{\forall j} R(tc'(j));$$

where Idose corresponds to a dose of previously-administered subcutaneous insulin, and tc represents a time since the administered does of subcutaneous insulin. $I_{effect}$ accordingly may correspond with an amount of insulin from a subcutaneous insulin dose that may be effective over a next time period (e.g. $t_{delta}$). In some examples, however, if the subcutaneous insulin dose was a dose of short-acting insulin, and the time since the administration of the dose exceeds a threshold for activity of the short-acting insulin (e.g. 300 minutes in one example), then $I_{effect}$ may be represented as zero (e.g. there is no further insulin-on-board due to the dose). Similarly, if the subcutaneous insulin dose was a dose of long-acting insulin, and the time since the administration of the dose exceeds a threshold for activity of the long-acting insulin (e.g. 36 hours in one example), then $I_{effect}$ may be represented as zero.

Figure 5:
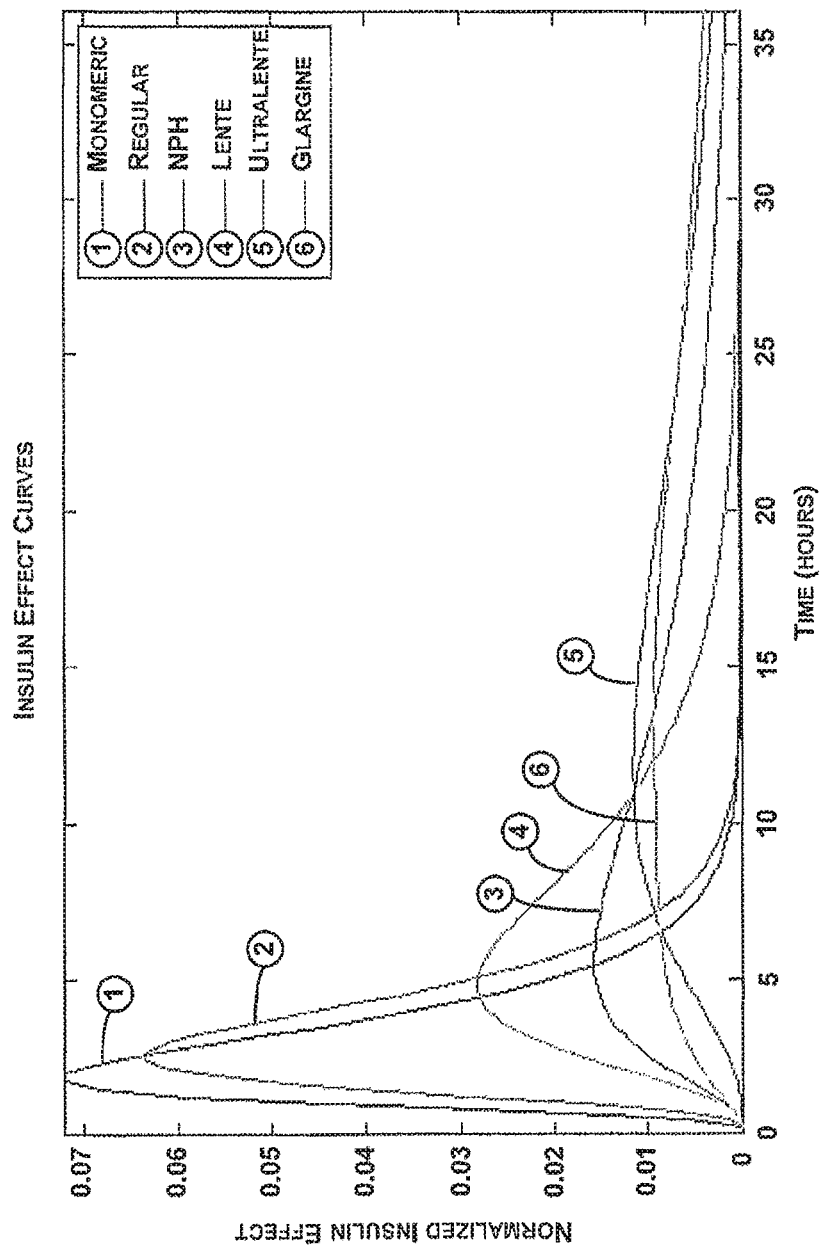
FIG. 5 is a plot representing example calculated insulin effect curves for six different types of insulin based upon example known pharmacokinetics.

FIG. 5 is a plot representing example calculated insulin effect curves for six different types of insulin based upon example known pharmacokinetics and the method described above (TS=15 minutes and GFR=100). The insulin effect curves may be calculated by programmed computing systems described herein in some examples, and/or may be provided to the computing systems for use in insulin dosing calculations described herein.

Referring back to FIG. 4, at block 412, the method 400 includes determining an amount of insulin-on board. For example, based on an estimate (or known) time of a prior administration of insulin, an amount of long-acting insulin-on-board can be estimated using the insulin effect curves.

At block 414, the method 400 includes determining an adjustment to the recommended insulin dosage. For example, an adjustment can be determined to compensate for short-acting insulin that is currently on board, changes in the patient's total daily dose that effect the expected long acting insulin-on-board and/or the non-uniform PK/PD curves associated with different types of insulin. An adjustment can be negative or positive. Adjustments may be made to recommended short-acting and long-acting insulin dosages, including subcutaneous doses, intravenous doses, or combinations thereof.

As an example, to determine an adjustment to the long-acting insulin dosage recommendation, an estimated long-acting insulin-on-board, $LA_{5\ hour}$, may be calculated (e.g. by the workstation 114 or system 104 of FIG. 1) according to:

$$LA_{5hour} = \left[\sum_{k=1}^{P} \sum_{j=rstart_k}^{rstop_k} LAused_k \cdot R(LAtype_k, j)\right] +$$

-continued $$\left[\sum_{j=1}^{5 \cdot (60/Ts)} LAused_{current} \cdot R(LAtype_{current}, j)\right] + I_{TPN} \times 5$$

where $$rstart_k = \text{round}\left(\frac{60}{Ts}(t_i - ti_k\ \text{hours})\right) + 1$$

$$rstop_k = \min\left(N_R, rstart_k + 5\frac{60}{Ts}\right),$$

$I_{TPN}$ is the rate of insulin infusion via TPN, $LAused_k$ and $SAused_k$ are associated confirmed (used) doses of long and short-acting insulin, $LAtype_k$ and $SAtype_k$ are associated indices specifying the type of long- and short-acting insulin administered, and $LAtype_{current}$ and $LAused_{current}$ are recommended long-acting insulin type and dose associated with the current event. During this same period an expected insulin-on-board may be determined (e.g. by the workstation and/or system 104 of FIG. 1) according to:

$$LA_{ideal} = LSDist_i \cdot TDD_i \cdot 5/24.$$

If the current TDD is not equal (or about equal) to the previous TDD, then the adjustment dose is determined to be the difference between the expected and estimated long-acting insulin on board:

$$SA_{adj,LA} = \begin{cases} LA_{ideal} - LA_{5hour} & TDD_i \ne TDD_{i-1} \\ 0 & \text{otherwise} \end{cases}.$$

As another example, to determine an adjustment for the short-acting insulin dosage recommendation, an estimated short-acting insulin-on-board, $SA_{5\ hour}$, includes the insulin following from prior doses:

$$SA_{5hour} = \left[\sum_{k=1}^{P} \sum_{j=rstart_k}^{rstop_k} SAused_k R(SAtype_k, j)\right]$$

where $$rstart_k = \text{round}\left(\frac{60}{Ts}(t_i - ti_k\ \text{hours})\right) + 1$$

$$rstop_k = \min\left(N_R, rstart_k + 5\frac{60}{Ts}\right)$$

Note that the recommended insulin associated with the current event is not included in this calculation, and the expected or ideal amount of short-acting insulin-on-board may be assumed to be zero.

The total adjustment dose, $SA_{adj}$, that will compensate for both long and short-acting insulin on board, can be determined according to the following:

$$SA_{adj} = SA_{adj,LA} - SA_{5\ hour}.$$

In the equation above, $SA_{adj,LA}$ is the estimated volume of long-acting insulin level that should be available over the next five hours. Other time intervals may be used in other examples. As noted previously, due to patient variability through time and/or previous sub-optimal estimates of long-acting insulin injections, the actual long-acting insulin on board may differ from the expected or optimal estimate. Specifically, the following situations may occur that impact $SA_{adj,LA}$:

If the patient's insulin requirements are unchanged, then $SA_{adj,LA}$ will be negative or positive depending on the PK/PD effect curve and will only compensate for the lack of uniform effectiveness through time. A non-zero value for $SA_{adj,LA}$ compensates for the non-uniform shape of the insulin action through time.

If the patient's insulin requirements have increased beyond what was estimated prior to the delivery of the last long-acting insulin volume, then $SA_{adj,LA}$ will be positive.

If the patients insulin requirements have decreased beyond what was previously estimated, then $SA_{adj,LA}$ will be negative.

In summary, $SA_{adj,LA}$ represents the difference between the future actual and ideal long-acting insulin on board. Because this volume is known, it can be used to adjust the short-acting insulin that is to be delivered whether or not the short-acting insulin dose is used for correction or meal coverage.

In another example, an intravenous (IV) dosing recommendation or adjustment to an IV dosing recommendation may be calculated in block 414 taking into account insulin-on-board, including insulin-on-board from previous or simultaneous subcutaneous insulin doses.

For example, an adjusted IV insulin bolus (e.g. short-acting insulin) dose may be calculated by subtracting the volume of short-acting subcutaneous insulin on board from a recommended or existing IV bolus volume. The adjusted IV insulin bolus dose may further in some examples be increased by an insulin volume sufficient to compensate for any entered carbohydrates. Accordingly, the adjusted IV insulin bolus dose ($I_{bolus\_adjust}$) may be expressed as:

$I_{bolus\_adjust} = I_{bolus} + I_{CS} - I_{effect,SA}$; where $I_{bolus}$ refers to an IV insulin bolus recommendation or dose, and $I_{CS}$ refers to an amount of IV or short-acting insulin required to compensate for any entered carbohydrates.

An adjusted IV delivery drip rate (e.g. long-acting insulin) may be calculated as a continuous infusion rate (e.g. units/hour) after converting and subtracting a long-acting insulin-on-board from an existing recommended or administered IV delivery rate. For example, the long-acting insulin volume calculated as insulin-on-board may be divided by a time between glucose measurements and subtracted from an existing recommended or administered IV drip rate. For example, the following equation may be used in some examples to calculate an adjusted IV insulin delivery rate ($I_{drip\_adjust}$):

$$I_{drip\_adjust} = I_{drip} - \frac{I_{effect,LA}}{(t_{delta}/60)};$$

where $I_{drop}$ refers to an existing recommended or administered IV insulin delivery rate (units/hour), $I_{effect,LA}$ refers to a volume of long-acting insulin on board, and $t_{data}$ refers to a time interval between glucose measurements. The factor of 60 is provided to convert the $t_{delta}$ into units commensurate with the delivery rates used, and is accordingly flexible based on the units employed in a given example.

The adjusted IV insulin bolus and continuous delivery doses may then be combined in accordance with the following examples:

If $I_{bolus\_adjust} < 0$ and $I_{drip\_adjust} > 0$ OR if $I_{bolus\_adjust} > 0$ and $I_{drip\_adjust} < 0$, OR if both are positive then a revised adjusted IV insulin recommendation may be generated for use in an IV dosing recommendation as follows:

$$I_{drip\_adjust} = I_{drip\_adjust} + \frac{I_{bolus\_adjust}}{(t_{delta}/60)}; \text{ and } I_{bolus\_adjust} = 0$$

Accordingly, examples of providing IV dosing recommendations or adjusted IV dosing recommendations in view of insulin on board (including insulin on board related to previous subcutaneous insulin doses), if an adjustment is warranted due to either an adjusted IV insulin bolus or continuous delivery rate recommendation being positive, the overall adjustment may be converted into an IV insulin continuous delivery rate for use in IV dosing.

Where $I_{drip\_adjust} < 0$ and $I_{bolus\_adjust} < 0$, then the IV insulin adjusted delivery rate may be 0 and a carbohydrate bolus may be recommended.

A user (e.g. nurse or IV dosing apparatus) may be provided with a revised IV dose as follows: $I_{drip,new} = I_{drip\_adjust}$ and $I_{bolus,new} = I_{bolus\_adjust}$. A recommended carbohydrate bolus may also or instead be provided if appropriate as described above. Accordingly, a drip rate and/or bolus volume may be altered based on insulin-on-bard calculations, including insulin-on-board due to previous or simultaneously administered subcutaneous insulin doses.

Figure 6:
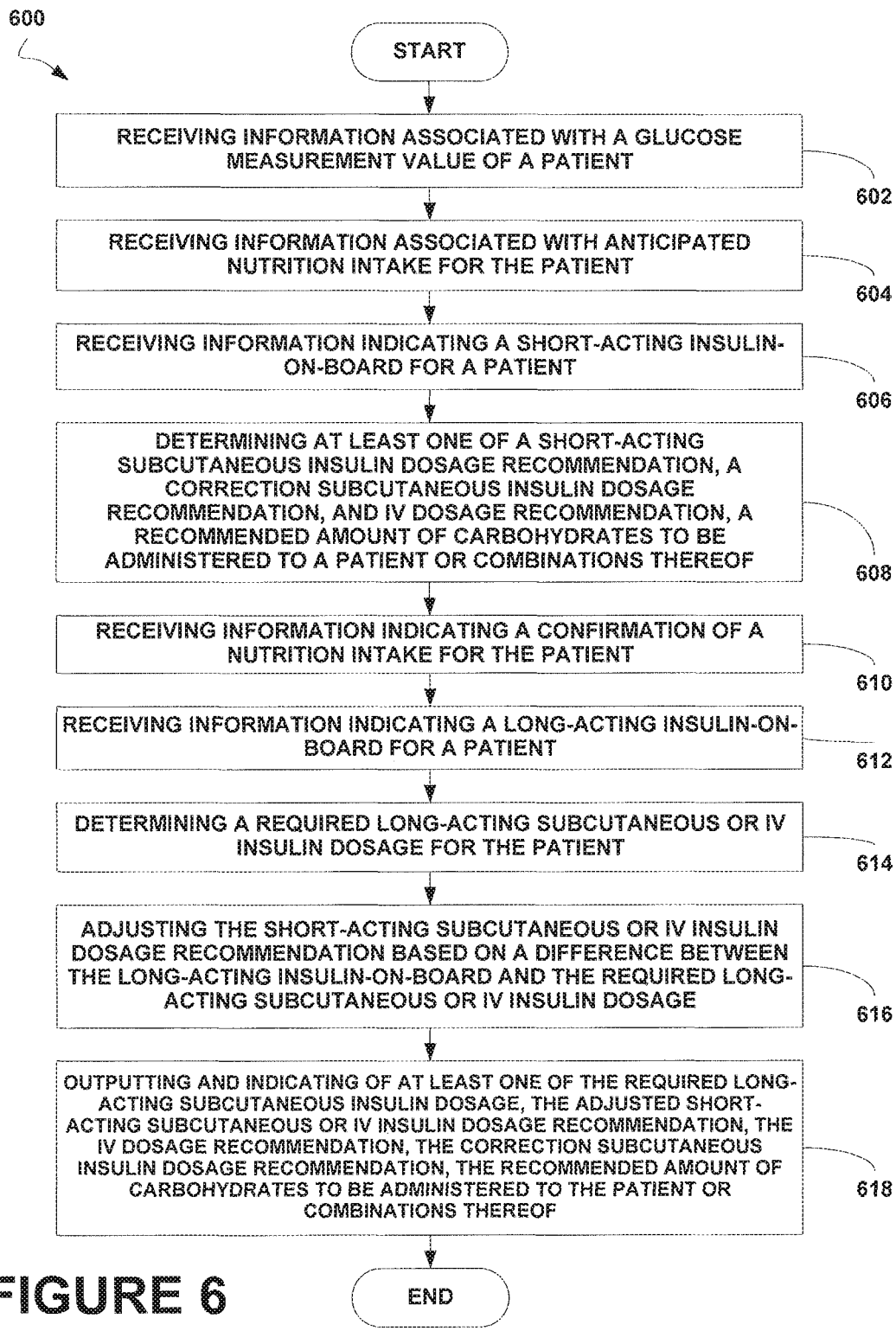
FIG. 6 is a block diagram of another example method to determine insulin therapy for a patient, in accordance with at least some embodiments described herein.

FIG. 6 is an example block diagram of another method to determine subcutaneous insulin therapy for a patient, in accordance with at least some embodiments described herein. Method 600 shown in FIG. 6 presents an embodiment of a method that, for example, could be used with the configuration shown in FIG. 1, for example, and may be performed by the system 104, the workstation 114, or a combination of the system 104 and the workstation 114. Method 600 may include one or more operations, functions, or actions as illustrated by one or more of blocks 602-618. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 602, the method 600 includes receiving information associated with a glucose measurement value of a patient. For example, a nurse may use a glucometer to determine a glucose measurement value of the patient, and the nurse may enter the glucose measurement value into a system. In other examples, the glucose measurement may be received by automated equipment and provided to a computing system implementing block 602 of the method 600.

The method 600 also includes receiving information associated with anticipated nutrition intake for the patient, at block 604. For example, a nurse may enter into a system the anticipated nutrition intake for the patient including any nutrition consumed orally, intravenously, or via feeding tubes. The information associated with the anticipated nutrition intake for the patient may include information indicating a timing and rate of a feeding tube, for example.

The method 600 also includes receiving information indicating a short-acting insulin-on-board for a patient, at block 606. Short-acting insulin-on-board may be associated with an amount of short-acting insulin that remains in the patient due to a prior insulin administration. A nurse may determine the short-acting insulin-on-board for the patient using many different methods (e.g., as described above in FIG. 4 and may enter the information into a system.

The method 600 also includes, at block 608, based on the information associated with the glucose measurement value of the patient, the anticipated nutrition intake for the patient and/or the short-acting insulin-on-board, determining at least one of a short-acting subcutaneous insulin dosage recommendation, a correction subcutaneous insulin dosage recommendation, an intravenous insulin dosage recommendation, a recommended amount of carbohydrates to be administered to the patient, or combinations thereof. For example, if the short-acting insulin-on-board is negative (e.g., too low), a recommended amount of carbohydrates can be determined to be administered to the patient. If the patient is about to consume a number of carbohydrates, a short-acting subcutaneous or IV insulin dosage may be recommended. If the glucose measurement value of the patient is not within a target range, a correction subcutaneous or IV insulin dosage may be recommended. In addition, based on the inputs received at blocks 602, 604, and 606, the recommendation may be to do nothing (e.g., if glucose values are within targets and no carbohydrates are anticipated to be ingested in the near future).

The method 600 also includes, at block 610, receiving information indicating a confirmation of a nutrition intake for the patient. For example, the nurse may confirm that the patient ingested the anticipated nutrition amounts, or may confirm the amount of nutrition that was administered to the patient. The nurse may input the confirmation information into a system and/or the information regarding nutrition intake may be provided by a food provider or other user of a system implementing the method 600.

The method 600 also includes, at block 612, receiving information indicating a long-acting insulin-on-board for a patient. Long-acting insulin-on-board may be associated with an amount of long-acting insulin that remains in the patient due to a prior insulin administration. In some examples, an amount of long-acting insulin may remain in a patient due to a previous or simultaneously administered subcutaneous insulin dose for a patient on or transitioning to IV insulin therapy. A nurse may determine the long-acting insulin-on-board for the patient using many different methods (e.g., as described above in FIG. 4), and may enter the information into a system. In other examples, the system may calculate the long-acting insulin-on-board as described above.

The method 600 also includes, at block 614, based on the information associated with the long-acting insulin-on-board for the patient, the glucose measurement value of the patient, and the confirmation of the nutrition intake for the patient, determining a long-acting subcutaneous or IV insulin dosage for the patient. For example, the long-acting subcutaneous insulin dosage may be determined based on anticipated needs of the patient.

The method 600 also includes, at block 616, adjusting the short-acting subcutaneous or IV insulin dosage recommendation based on a difference between the long-acting insulin-on-board and the required long-acting subcutaneous or IV insulin dosage. For example, if the difference between the long-acting insulin-on-board and the required long-acting subcutaneous or IV insulin dosage is large and the long-acting insulin-on-board is more than the required long-acting insulin dosage, then there remains an excess amount of long-acting insulin-on-board and the short-acting subcutaneous insulin dosage recommendation may be lowered. Alternatively, if the difference between the long-acting insulin-on-board and the required long-acting subcutaneous or IV insulin dosage is large and the long-acting insulin-on-board is less than the required long-acting insulin dosage, then short-acting subcutaneous or IV insulin dosage recommendation may be increased (depending on the amount of long-acting insulin to be administered).

Still further, if the difference between the long-acting insulin-on-board and the required long-acting subcutaneous or IV insulin dosage is small and the long-acting insulin-on-board is more than the required long-acting insulin dosage, then there remains an excess amount of long-acting insulin-on-board and the short-acting subcutaneous or IV insulin dosage recommendation may be lowered. Similarly, if the difference between the long-acting insulin-on-board and the required long-acting subcutaneous or IV insulin dosage is small and the long-acting insulin-on-board is less than the required long-acting insulin dosage, then the short-acting subcutaneous or IV insulin dosage recommendation may also be lowered.

The method 600 also includes, at block 618, outputting an indication of at least one of the required long-acting subcutaneous insulin dosage, the adjusted short-acting subcutaneous or IV insulin dosage recommendation, the IV dosage recommendation, the correction subcutaneous insulin dosage recommendation, the recommended amount of carbohydrates to be administered to the patient, or combinations thereof. For example, any of this information may be output onto a display, such as for example, within a graphical user interface (GUI).

The method 600 may be performed in the order as shown in blocks 602-616, or in other orders, such as by receiving information and following performing determination steps.

In addition, the method 600 may include additional steps not shown. For example, the method 600 may include receiving information indicating a confirmation of a last insulin dose given subcutaneously to the patient so as to determine when a last dosage was given and an amount given. As another example, other information such as demographics of a patient and a serum creatinine level of the patient may be received, and a glomerular filtration rate (GFR) of the patient can be determined based on the demographics and the serum creatinine level of the patient. As further examples, information indicating a total daily dosage amount for the patient of short-acting insulin and long-acting insulin can be received, as well as information indicating drugs administered to the patient including one or steroids and antibiotics. As still further examples, information indicating whether a postprandial emesis has occurred, information indicating intravenous (IV) therapy provided to the patient, and information indicating total parenteral nutrition (TPN) provided to the patient can be received. Insulin dosages can then be determined taking into account any of this additional information.

Figure 7:
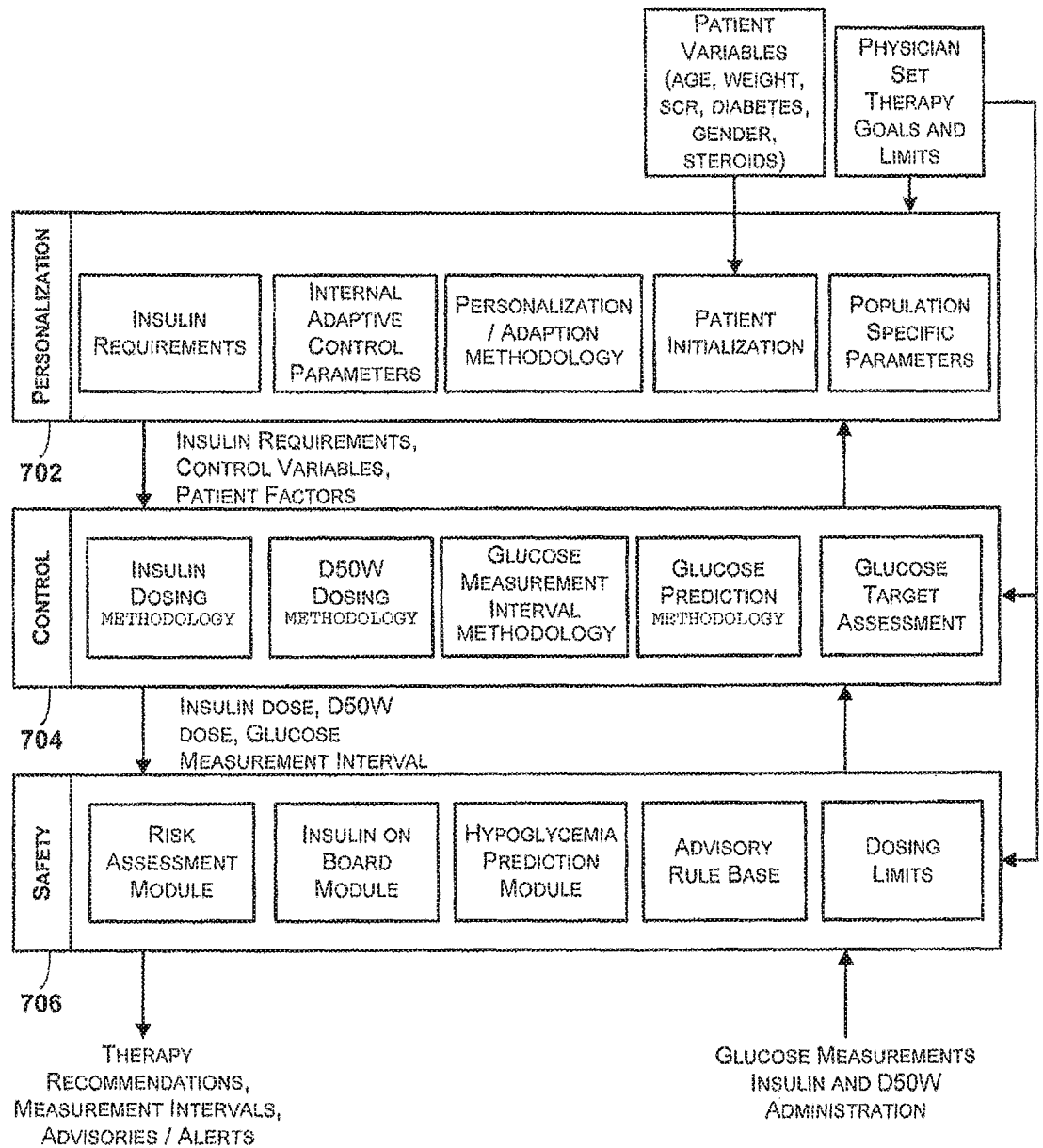
FIG. 7 is a block diagram illustrating an example flow of information to estimate insulin-on-board determinations and adjustments to insulin recommendations.

FIG. 7 is a block diagram illustrating an example architecture of processing modules and information flow of a glucose management system that includes a safety component to estimate insulin-on-board determinations and adjustments to insulin recommendations. The information may include personalization information 702, control information 704, and safety information 706. Personalization information 702 may include, but is not limited to, information per patient such as insulin requirements, internal adaptive control parameters describing an insulin therapy according to an adaption algorithm, patient initialization information (age, weight, SCR, diabetes type, gender, steroid usage, etc.), and population specific parameters. Control information 704 may include, but is not limited to, insulin dosing methodologies, D50W dosing methodologies, glucose measurement interval methodologies, glucose prediction methodologies, and glucose target assessments. Safety information 706 may include, but is not limited to, risk assessment modules, insulin-on-board modules, hypoglycemia prediction modules, an advisory rule base, and dosing limits.

Based on the personalization information 702, the control information 704, and the safety information 706, therapy recommendations, measurement intervals, advisories and alerts may be determined, for example, according to the methods described herein.

In one embodiment, a computerized system is provided for adapting an existing insulin regimen according to diet changes or other factors described herein. A user may enter a modified diet and the system may provide a new insulin regimen. The system may operate using a graphical user interface (GUI) to display events in a chronological manner such that nurses or other users can easily determine patient state. The GUI may be provided in as an interrogative interface in which the GUI provides specific requests for additional information when glucose values are unexpected/unanticipated. The computerized system provides a mechanism for transferring patient specific estimated control variables to and from IV insulin dosing tools, and may be used within a hospital setting or as an at-home use module to determine treatment decisions and calculation of subcutaneous insulin dosages.

Figure 8:
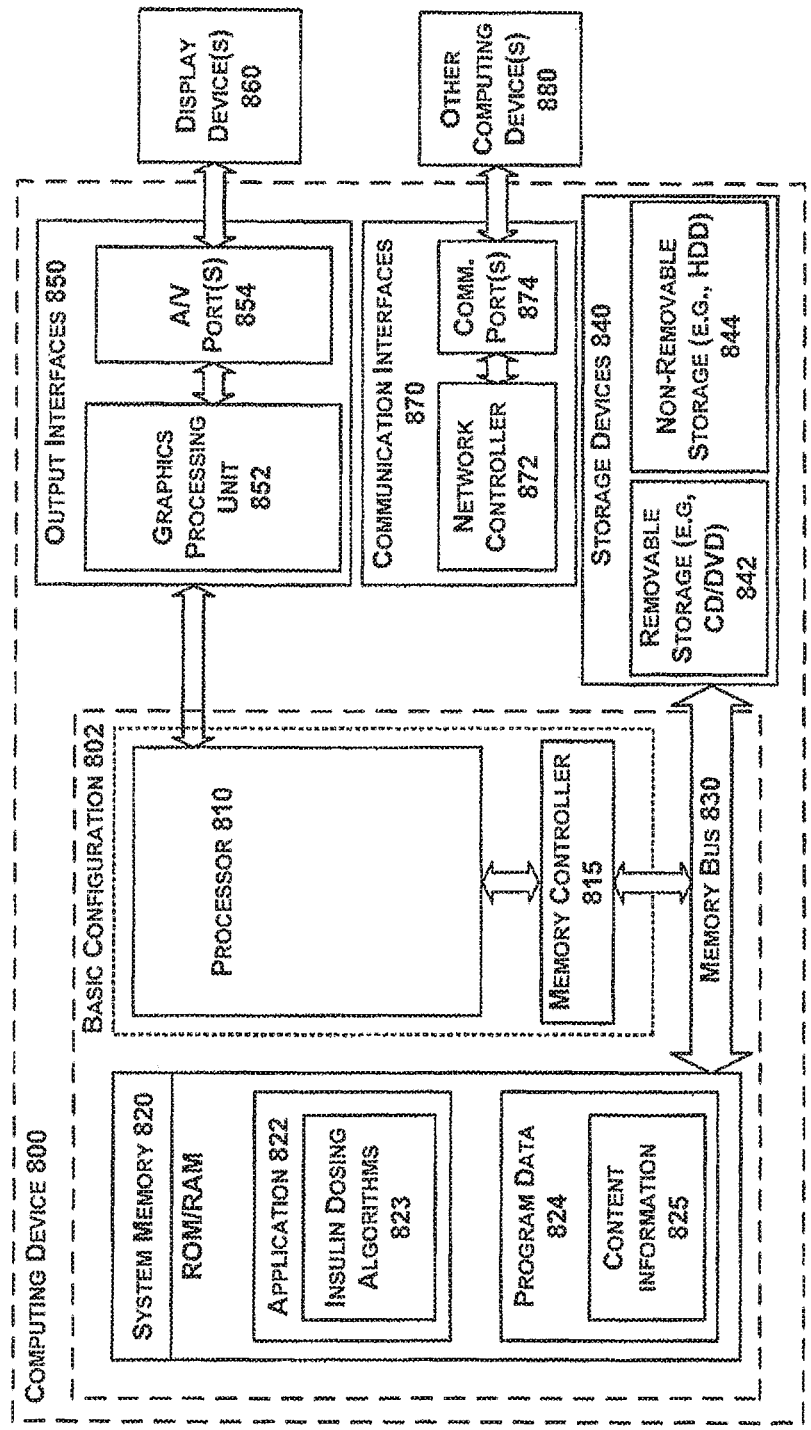
FIG. 8 is a functional block diagram illustrating an example computing device used in a computing system that is arranged in accordance with at least some embodiments described herein.

FIG. 8 is a functional block diagram illustrating an example computing device 800 used in a computing system that is arranged in accordance with at least some embodiments described herein. The computing device may be a personal computer or mobile device, and may be implemented as one of the components FIGS. 1 and 3, for example, such as the workstation 114, or all or a component of the system 104, such as the application server 108. In one configuration 802, computing device 800 may typically include one or more processors 810 and system memory 820. A memory bus 830 may be used for communicating between the processor 810 and the system memory 820. Depending on the desired configuration, processor 810 can be of any type including but not limited to a microprocessor (μP), a microcontroller (μC), a digital signal processor (DSP), or any combination thereof. A memory controller 815 can also be used with the processor 810, or in some implementations, the memory controller 815 can be an internal part of the processor 810.

Depending on the desired configuration, the system memory 820 can be of any type including but not limited to volatile memory (such as RAM), non-volatile memory (such as ROM, flash memory, etc.) or any combination thereof. System memory 820 may include one or more applications 822, and program data 824, Application 822 may include instructions for insulin dosage recommendations 823 that are arranged to implement insulin dosing methodologies described herein, and may provide inputs to the electronic circuits, in accordance with the present disclosure. Program Data 824 may include content information 825 that could be directed to any number of types of data as described in FIG. 7, for example. In some example embodiments, application 822 can be arranged to operate with program data 824 on an operating system.

Computing device 800 can have additional features or functionality, and additional interfaces to facilitate communications between the basic configuration 802 and any devices and interfaces. For example, data storage devices 840 can be provided including removable storage devices 842, non-removable storage devices 844, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Computer storage media can include volatile and nonvolatile, non-transitory, removable and non-removable media implemented in any method or technology for storage of information, such as computer readable instructions, data structures, program modules, or other data.

System memory 820 and storage devices 840 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media can be part of device 800.

Computing device 800 can also include output interfaces 850 that may include a graphics processing unit 852, which can be configured to communicate to various external devices such as display devices 860 or speakers via one or more A/V ports or a communication interface 870. The communication interface 870 may include a network controller 872, which can be arranged to facilitate communications with one or more other computing devices 880 over a network communication via one or more communication ports 874. The communication connection is one example of a communication media, Communication media may be embodied by computer readable instructions, data structures, program modules, or other data in a modulated data signal, such as a carrier wave or other transport mechanism, and includes any information delivery media. A modulated data signal can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR), cellular, and other wireless media.

Computing device 800 can be implemented as a portion of a small-form factor portable (or mobile) electronic device such as a cell phone, tablet, a personal data assistant (PDA), a personal media player device, a wireless web-watch device, a personal headset device, an application specific device, or a hybrid device that include any of the above functions. Computing device 800 can also be implemented as a personal computer including both laptop computer and non-laptop computer configurations.

Figure 9A:
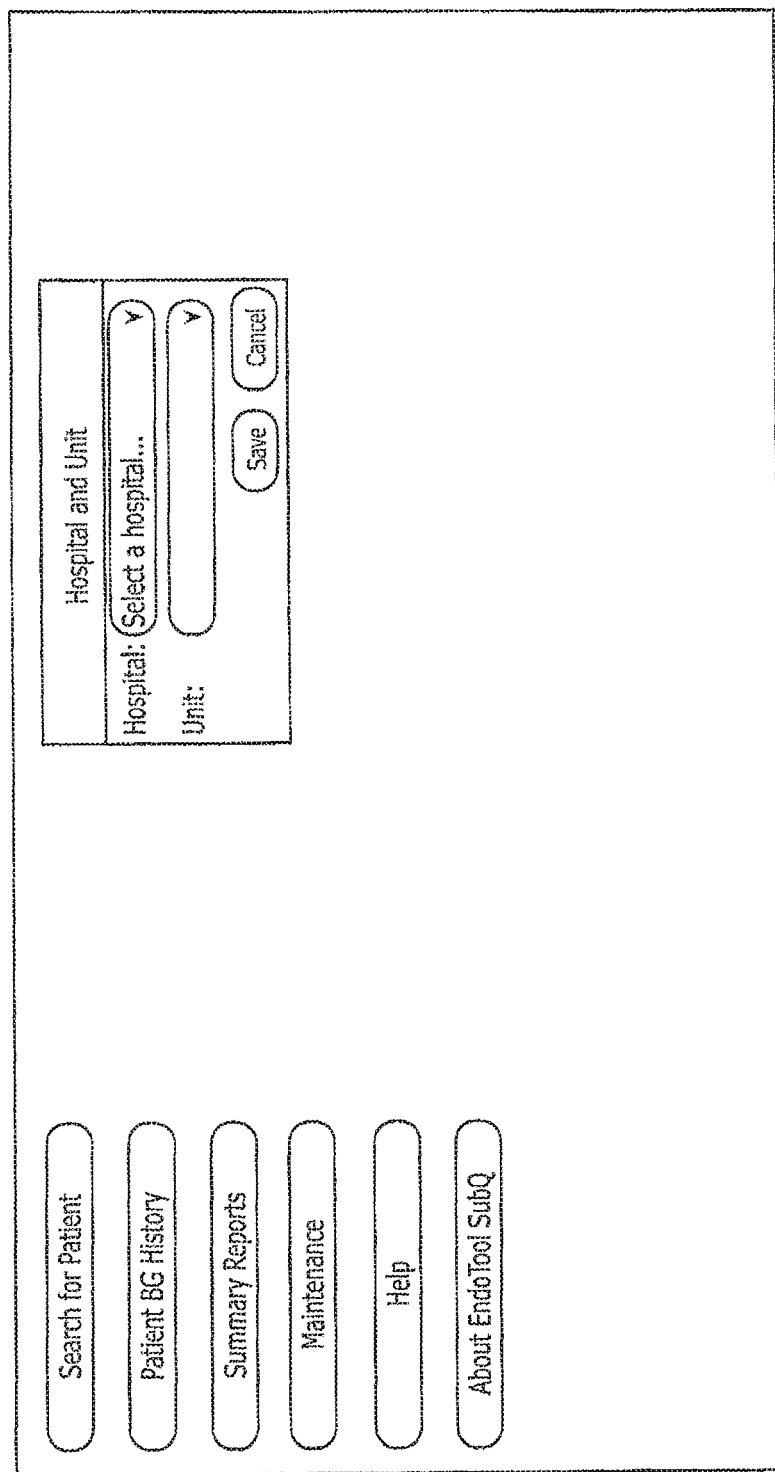
Figure 9B:
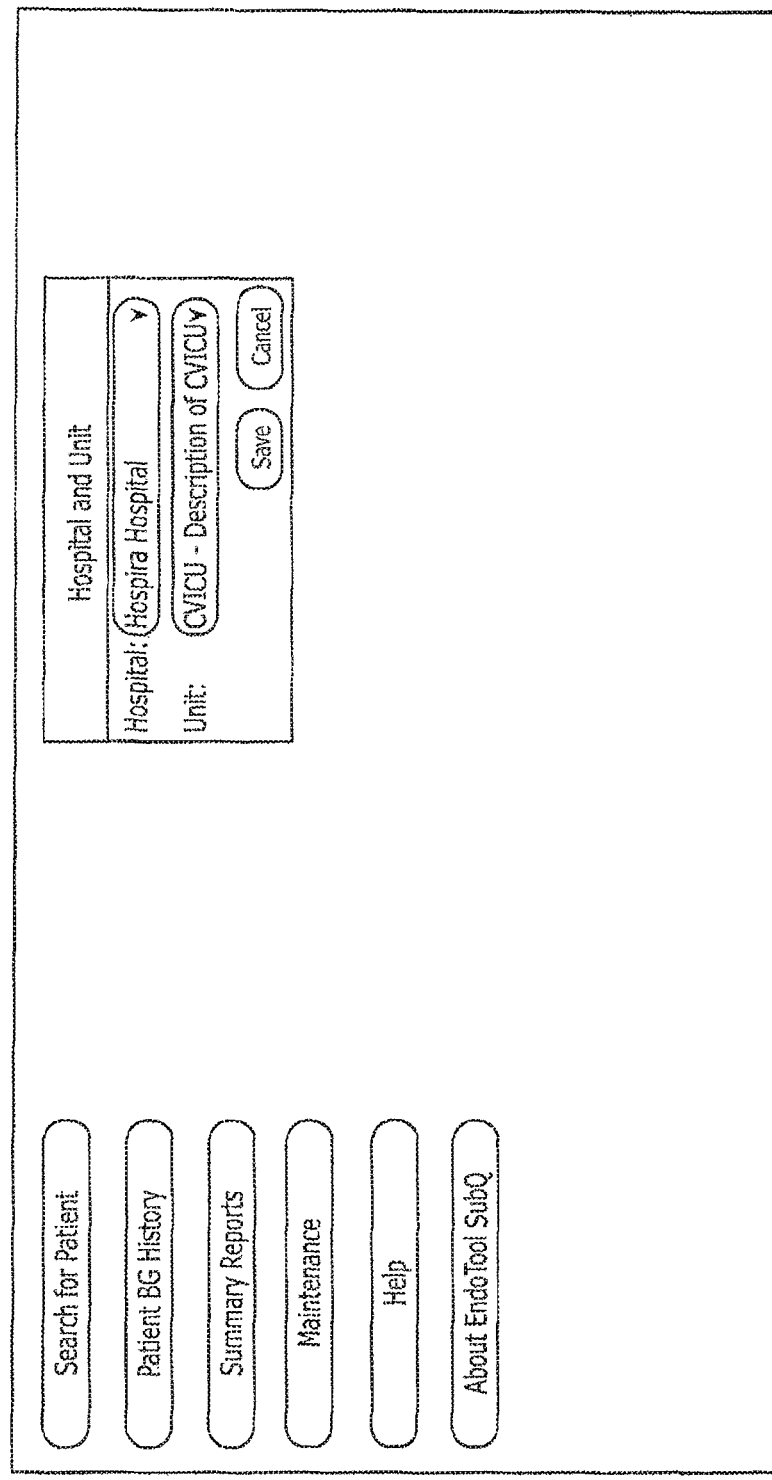

FIGS. 9A-9L illustrate example GUIs that may be implemented on a computing device or computing system to receive and display information according to embodiments disclosed herein. Initially, a user may login to a server and be presented with an interface similar to that shown in FIG. 9A. A user may select a hospital and unit, as shown in FIG. 9B, and may be presented with GUIs customized to the selected hospital and unit parameters, for example. Additional information may be presented for selection at the startup screen including a glucose measurement schedule, an insulin therapy schedule, and a nutritional plan, and GUIs may be presented that are customized according to the protocol selected.

Figure 9C:
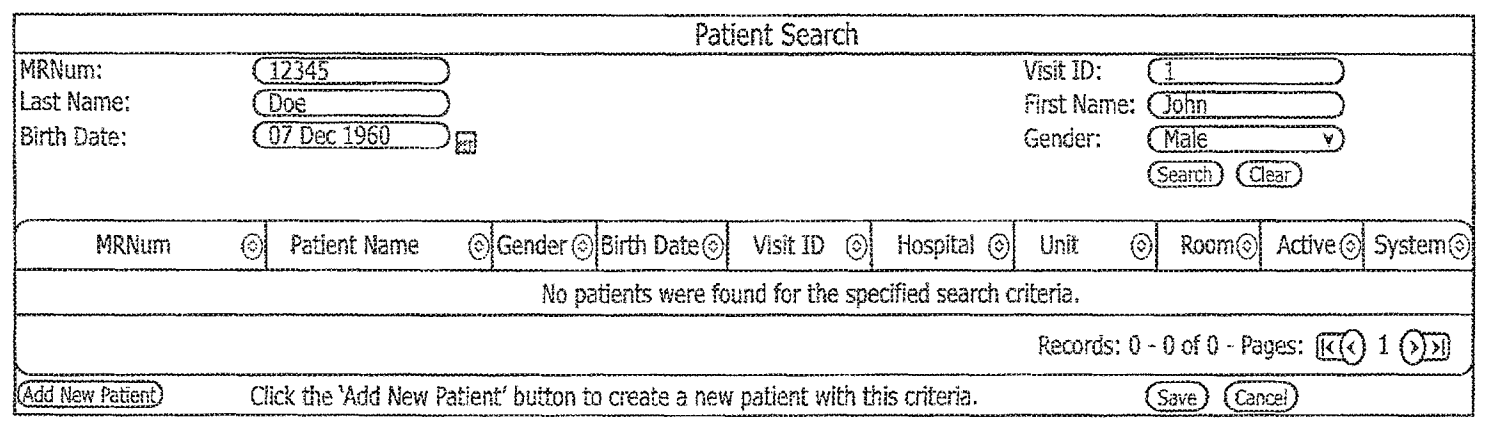

A user may then perform a search for information associated with a patient, and may be presented with an interface as shown in FIG. 9C. Any number or kind of information may be presented, such as a medical record number, name, birth date, gender, hospital room, etc.

Figure 9D:
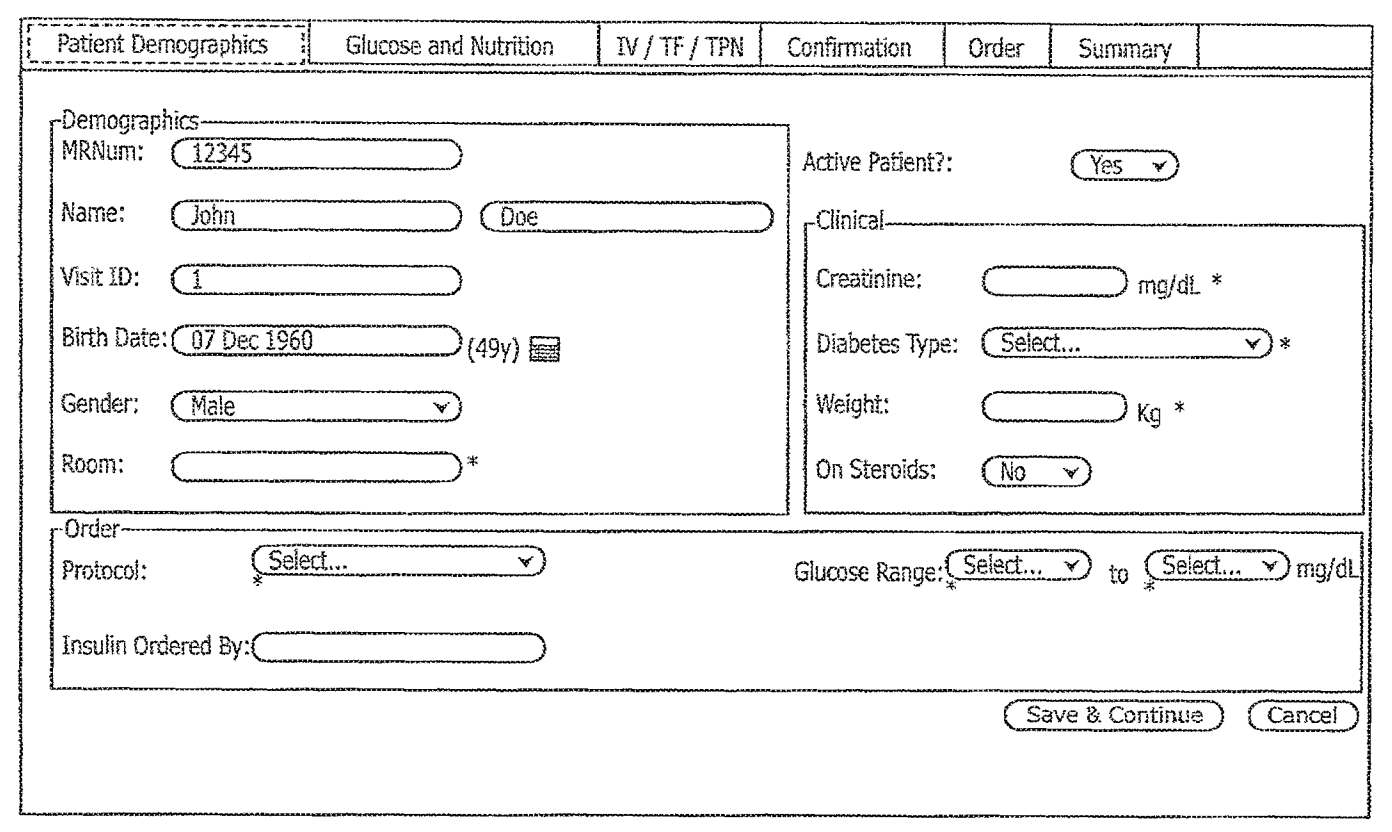

Additional information associated with the patient may be accessed through a tabbed GUI as shown in FIG. 9D. For example, the interface in FIG. 9D illustrates six tabs labeled. Patient Demographics, Glucose and Nutrition, IV/TF/TPN, Confirmation, Order, and Summary. More or fewer tabs may be presented. FIG. 9D illustrates the Patient Demographics tab highlighted and selected, in which general patient information is displayed. A nurse or other user may retrieve such information by inputting the patient's medical record number, or by direct input.

Figure 9F:
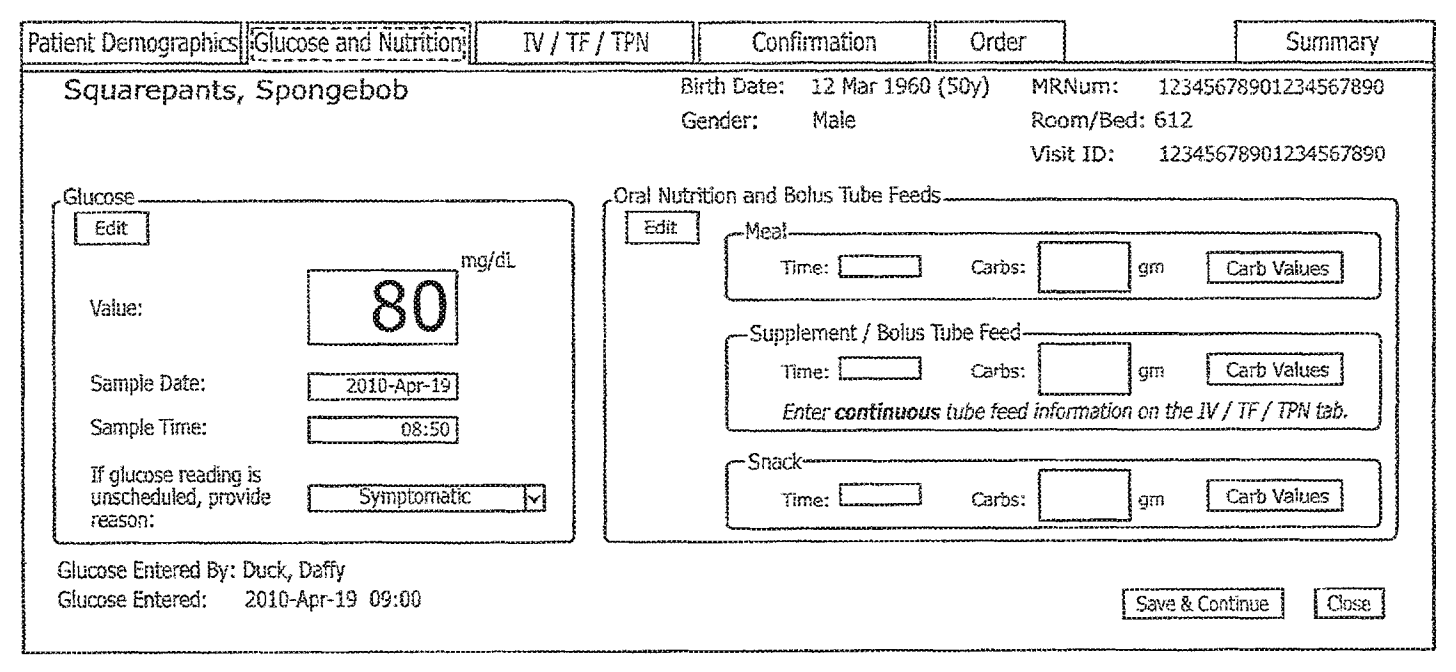

Within FIG. 9D, a nurse or other user may enter glucose dosage information. Similarly, the nurse or other user may access a GUI as shown in FIG. 9E to enter glucose dosage information of a patient including prior glucose therapy administered, and last dosage times and amounts for short-acting and long-acting insulin, for example. The nurse or other user may access further information regarding glucose and nutrition by selecting the glucose and nutrition tab, as shown by the GUI in FIG. 9F. In FIG. 9F, the nurse or other user may enter last glucose dosages, as well as information regarding anticipated nutrition intake including times and carbohydrate amounts. Values for carbohydrates can be determined using a lookup function, as shown by the GUI in FIG. 9G, for example.

Figure 9H:
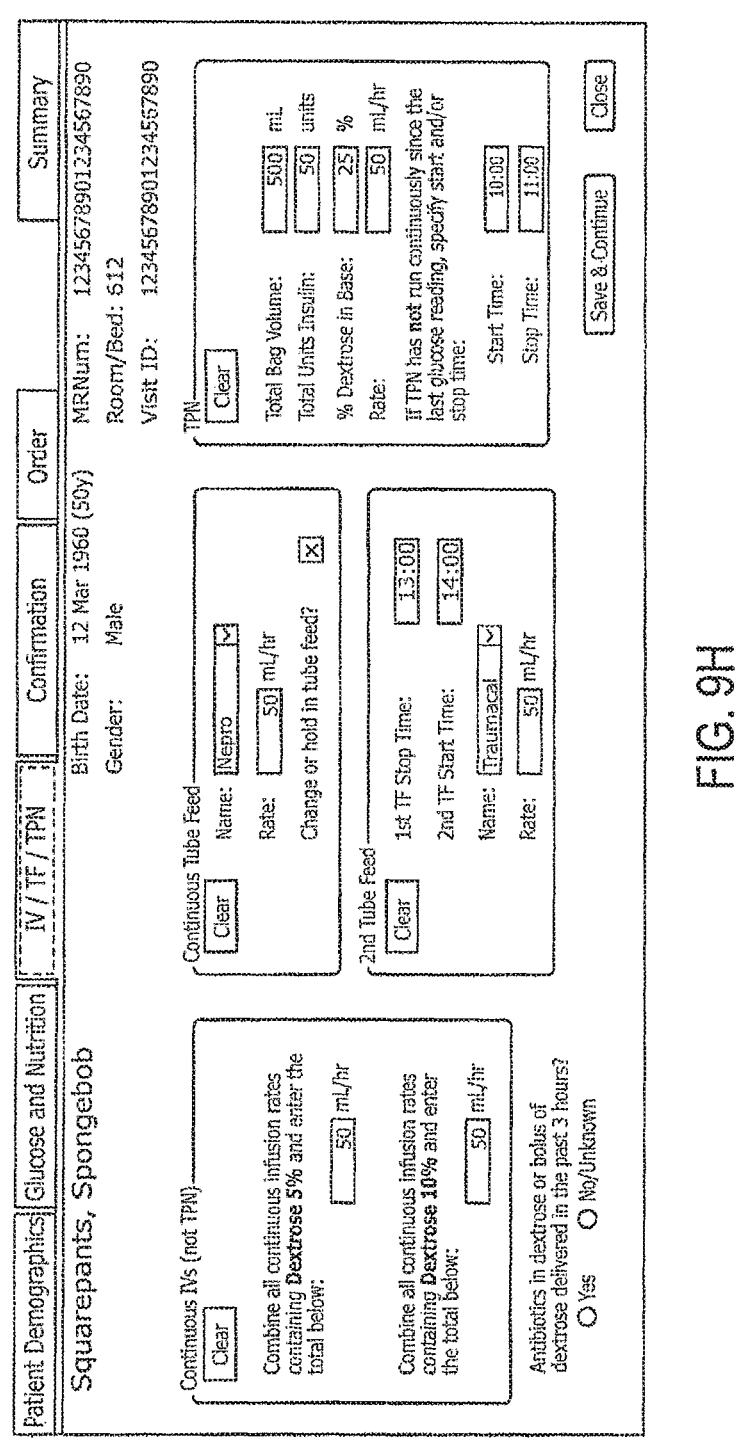

FIG. 9H illustrates information provided by selecting the Intravenous (IV)/Tube Feeding (TF)/Total Parenteral Nutrition (TPN) tab. In this interface, a nurse or other user may enter or determine information associated with any other IVs provided to the patient, whether the patient is on antibiotics, whether the patient is receiving any tube feeding, and information associated with TPN in general.

FIG. 9I illustrates information provided by selecting the Confirmation tab. In this GUI, a nurse or other user may confirm information that has been entered including glucose dosages as well as actual nutrition consumed (as compared to previously entered anticipated nutritional intake).

FIGS. 9J and 9K are examples of information that may be provided by selecting the Order tab. In FIG. 9J, and example recommendation for glucose dosages are provided. An amount of long-acting insulin, meal coverage insulin (e.g., short-acting insulin), and correction insulin are recommended to be administered to the patient. A glucose value is also provided, and due to the glucose value being high, a recommendation is made to check the glucose value of the patient again in two hours, for example. FIG. 9K illustrates another example of a received recommendation in which a recommendation is made for an amount of carbohydrates to be administered to the patient since the glucose value was low. Also, since the glucose value was low, a recommendation is made to check the glucose value again in 15 minutes.

Figure 9L:
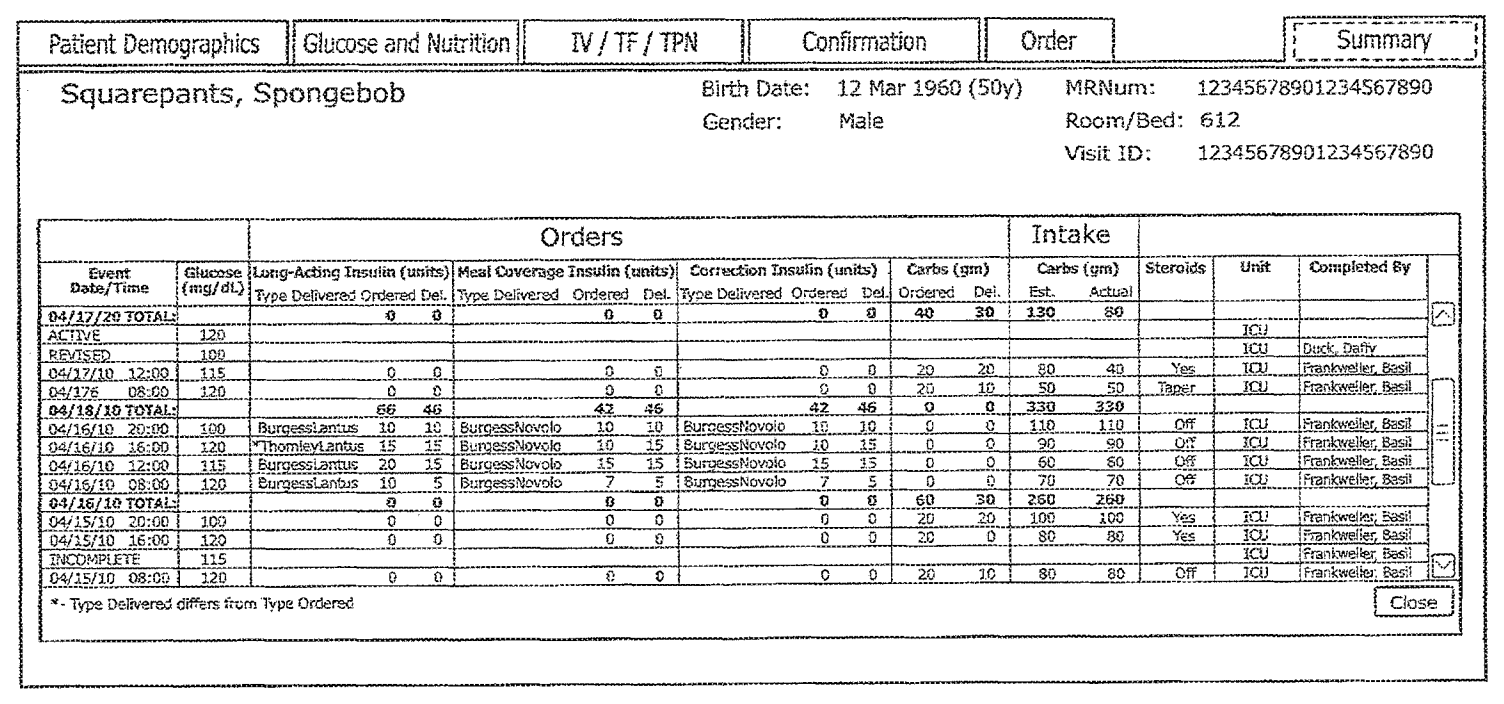

FIG. 9L illustrates example information that is provided by selecting the Summary tab. In this GUI, glucose measurements, glucose orders, and carbohydrate intakes can be seen in a table format to illustrate a medical history and status of the patient, for example.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

Additionally, although the specification refers primarily to short and long-acting insulin types, the invention contemplates and is applicable to more specific categories of insulin types including rapid-acting, short acting, intermediate acting, long acting, and insulin mixtures. Further, the invention anticipates the use of specific insulins or insulin analogs beyond those listed in the examples, including the modification of IV insulin, dosed for remediation of hyperglycemia, on the basis of all types of insulin on board.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A non-transitory computer readable medium having stored therein instructions executable by a computing device to cause the computing device to perform functions comprising: adjusting a short-acting subcutaneous insulin dosage recommendation or an intravenous insulin dosage recommendation for a patient based on a difference between a long-acting subcutaneous insulin-on-board measurement acquired from the patient and a required long-acting subcutaneous insulin dosage, or based on an insulin-on-board measurement remaining from a short-acting subcutaneous insulin dosage, or based on an insulin-on-board measurement remaining from an intravenous insulin dosage, such that: the short-acting subcutaneous insulin dosage recommendation or the intravenous insulin dosage recommendation is lowered if the difference between the long-acting subcutaneous insulin-on-board measurement and the required long-acting subcutaneous insulin dosage is more than a predetermined value and the long-acting subcutaneous insulin-on-board measurement is greater than the required long-acting subcutaneous insulin dosage, or the insulin-on-board measurement remaining from the short-acting subcutaneous insulin dosage is more than the predetermined value, or the insulin-on-board measurement remaining from the intravenous insulin dosage is more than the predetermined value, or the insulin-on-board measurement remaining from short-acting subcutaneous insulin dosage has a positive value or the insulin-on-board measurement remaining from the intravenous insulin dosage has a positive value; and the short-acting subcutaneous insulin dosage recommendation or the intravenous insulin dosage recommendation is increased if the difference between the long-acting subcutaneous insulin-on-board measurement and the required long-acting subcutaneous insulin dosage is less than the predetermined value, or the insulin-on-board measurement remaining from the short-acting subcutaneous insulin dosage is less than the predetermined value, or the insulin-on-board measurement remaining from the intravenous insulin dosage is less than the predetermined value, or the insulin-on-board measurement remaining from the short-acting subcutaneous insulin dosage has a negative value, or the insulin-on-board measurement remaining from the intravenous insulin dosage has a negative value; and outputting an indication of the short-acting subcutaneous recommendation or the intravenous insulin dosage recommendation.

2. The non-transitory computer readable medium of claim 1, wherein the instructions are executable to cause the computing device to further perform the functions comprising: receiving a patient physiological characteristic indication from a measuring unit, wherein the patient physiological characteristic indication comprises a body weight, a body height, a gender, an age, a type of Diabetes Mellitus, an activity level, a measure of kidney filtration such as a serum creatinine measurement result, a blood-glucose level, or combinations thereof prior to t adjusting of the short-acting subcutaneous insulin dosage recommendation or the intravenous insulin dosage recommendation.

3. The non-transitory computer readable medium of claim 1, wherein the outputting of the indication of the short-acting subcutaneous recommendation or the intravenous insulin dosage recommendation comprises displaying the indication on an interactive display.

4. The non-transitory computer readable medium of claim 1, wherein the outputting of the indication of the short-acting subcutaneous recommendation or the intravenous insulin dosage recommendation comprises providing the indication to an input unit, the input unit configured to administer the short-acting subcutaneous recommendation or the intravenous insulin dosage recommendation to the patient.

5. The non-transitory computer readable medium of claim 1, wherein the instructions are executable to cause the computing device to further perform the functions comprising: determining an estimated glomerular filtration rate (eGFR) of the patient based, at least in part, on a demographic and a serum creatinine level of the patient.

6. The non-transitory computer readable medium of claim 1, wherein the instructions are executable to cause the computing device to further perform the functions comprising: determining a correction subcutaneous insulin dosage recommendation when a received glucose measurement value of the patient is not within a target range.

7. The non-transitory computer readable medium of claim 1, wherein the instructions are executable to cause the computing device to further perform the functions comprising: disseminating an order embodying the indication of the short-acting subcutaneous recommendation or the intravenous insulin dosage recommendation to various locations within a hospital equipped to execute the order.

8. The non-transitory computer readable medium of claim 1, wherein the instructions are executable to cause the computing device to further perform the functions comprising: receiving a static input, a glucometer input, and a drug input prior to the adjusting of the short-acting subcutaneous insulin dosage recommendation or the intravenous insulin dosage recommendation.

9. The non-transitory computer readable medium of claim 8, wherein the static input comprises an indication of a diabetes control method used by the patient, an institutional parameter specific to a hospital, a renal status of the patient, or combinations thereof.

10. The non-transitory computer readable medium of claim 8, wherein the glucometer input comprises a blood glucose value obtained from a glucometer at a point-of-care.

11. The non-transitory computer readable medium of claim 8, wherein the drug input comprises previously confirmed administrated dosages of a subcutaneous insulin or an intravenous insulin confirmed dosage, a predicted or actual enteral or parenteral carbohydrate ingested by the patient, an indication of a dextrose intravenous drug administered to the patient, an indication of a steroid administered to the patient, an indication of an anticipated or actual activity level of the patient, an indication of an emesis by the patient, an indication of a previous or simultaneous subcutaneous insulin dosage administered to the patient, or combinations thereof.

12. A method for determining a patient therapy, the method comprising: adjusting a short-acting subcutaneous insulin dosage recommendation or an intravenous insulin dosage recommendation for a patient based on a difference between a long-acting subcutaneous insulin-on-board measurement acquired from the patient and a required long-acting subcutaneous insulin dosage, or based on an insulin-on-board measurement remaining from a short-acting subcutaneous insulin dosage, or based on an insulin-on-board measurement remaining from an intravenous insulin dosage, such that: the short-acting subcutaneous insulin dosage recommendation or the intravenous insulin dosage recommendation is lowered if the difference between the long-acting subcutaneous insulin-on-board measurement and the required long-acting subcutaneous insulin dosage is more than a predetermined value and the long-acting subcutaneous insulin-on-board measurement is greater than the required long-acting subcutaneous insulin dosage or the insulin-on-board measurement remaining from the short-acting subcutaneous insulin dosage is more than the predetermined value, or the insulin-on-board measurement remaining from the intravenous insulin dosage is more than the predetermined value, or the insulin-on-board measurement remaining from short-acting subcutaneous insulin dosage has a positive value or the insulin-on-board measurement remaining from the intravenous insulin dosage has a positive value; and the short-acting subcutaneous insulin dosage recommendation or the intravenous insulin dosage recommendation is increased if the difference between the long-acting subcutaneous insulin-on-board measurement and the required long-acting subcutaneous insulin dosage is less than the predetermined value or the insulin-on-board measurement remaining from the short-acting subcutaneous insulin dosage is less than the predetermined value or insulin-on-board measurement remaining from the intravenous insulin dosage is less than the predetermined value or the insulin-on-board measurement remaining from the short-acting subcutaneous insulin dosage has a negative value or the insulin-on-board measurement remaining from the intravenous insulin dosage has a negative value; and outputting an indication of the short-acting subcutaneous recommendation or the intravenous insulin dosage recommendation.

13. The method of claim 12, further comprising receiving a patient physiological characteristic indication from a measuring unit, wherein the patient physiological characteristic indication comprises a body weight, a body height, a gender, an age, a type of Diabetes Mellitus, an activity level, a measure of kidney filtration such as a serum creatinine measurement result, a blood-glucose level, or combinations thereof.

14. The method of claim 12, wherein the outputting of the indication of the short-acting subcutaneous recommendation or the intravenous insulin dosage recommendation comprises displaying the indication on an interactive display or providing the indication to an input unit, the input unit configured to administer the short-acting subcutaneous recommendation or the intravenous insulin dosage recommendation to the patient.

15. The method of claim 12, further comprising disseminating an order embodying the indication of the short-acting subcutaneous recommendation or the intravenous insulin dosage recommendation to various locations within a hospital equipped to execute the order.

16. The method of claim 12, further comprising receiving a static input, a glucometer input, and a drug input prior to the adjusting of the short-acting subcutaneous insulin dosage recommendation or the intravenous insulin dosage recommendation.

17. The method of claim 16, wherein the static input comprises an indication of a diabetes control method used by the patient, an institutional parameter specific to a hospital, a renal status of the patient, or combinations thereof.

18. The method of claim 16, wherein the drug input comprises previously confirmed administrated dosages of a subcutaneous insulin or an intravenous insulin confirmed dosage, a predicted or actual enteral or parenteral carbohydrate ingested by the patient, an indication of a dextrose intravenous drug administered to the patient, an indication of a steroid administered to the patient, an indication of an anticipated or actual activity level of the patient, an indication of an emesis by the patient, an indication of a previous or simultaneous subcutaneous insulin dosage administered to the patient, or combinations thereof.

19. A non-transitory computer readable medium having stored therein instructions executable by a computing device to cause the computing device to perform functions comprising: adjusting a short-acting subcutaneous insulin dosage recommendation for a patient based on a difference between a long-acting subcutaneous insulin-on-board measurement acquired from the patient and a required long-acting subcutaneous insulin dosage or an insulin-on-board measurement remaining from a short-acting subcutaneous insulin dosage, such that: the short-acting subcutaneous insulin dosage recommendation is lowered if the difference between the long-acting subcutaneous insulin-on-board measurement and the required long-acting subcutaneous insulin dosage is more than a predetermined value and the long-acting subcutaneous on-board measurement is greater than the required long-acting subcutaneous insulin dosage or the insulin-on-board measurement remaining from the short-acting subcutaneous insulin dosage is more than a predetermined value, or the insulin-on-board measurement remaining from the short-acting subcutaneous insulin dosage has a positive value; and the short-acting subcutaneous insulin dosage recommendation is increased if the difference between the long-acting subcutaneous insulin-on-board measurement and the required long-acting subcutaneous insulin dosage is less than the predetermined value, or the insulin on board measurement remaining from the short-acting subcutaneous insulin dosage is less than the predetermined value, or the insulin-on-board remaining from the short-acting subcutaneous insulin dosage is a negative value; and outputting an indication of the short-acting subcutaneous recommendation.

20. A non-transitory computer readable medium having stored therein instructions executable by a computing device to cause the computing device to perform functions comprising: adjusting an intravenous insulin dosage recommendation for a patient based on an insulin-on-board measurement from an intravenous insulin dosage, such that: the intravenous insulin dosage recommendation is lowered if the insulin-on-board measurement from the intravenous insulin dosage is more than a predetermined value; and the intravenous insulin dosage recommendation is increased if a different between the insulin-on-board measurement from the intravenous insulin dosage and an insulin-on-board required to reach a targeted intravenous insulin dosage is more than the predetermined value and the insulin-on-board required to reach the targeted intravenous insulin dosage has a positive value; and outputting an indication of the intravenous insulin dosage recommendation.

\* \* \* \* \*